(12) United States Patent
Bartels et al.

(10) Patent No.: US 8,796,471 B2
(45) Date of Patent: Aug. 5, 2014

(54) PROCESS FOR THE PREPARATION OF PROLINE DERIVATIVES

(71) Applicant: Hoffmann-La Roche Inc., Nutley, NJ (US)

(72) Inventors: Bjoern Bartels, Schopfheim (DE); Fritz Bliss, Hartheim (DE); Philipp Cueni, Basel (CH); Christophe Pfleger, Mulhouse (FR); Ulrich Zutter, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 13/671,586

(22) Filed: Nov. 8, 2012

(65) Prior Publication Data
US 2013/0123512 A1    May 16, 2013

(30) Foreign Application Priority Data

Nov. 11, 2011 (EP) .................................... 11188728

(51) Int. Cl.
*C07D 207/09*    (2006.01)
(52) U.S. Cl.
CPC ................................ *C07D 207/09* (2013.01)
USPC ...................................................... 548/537
(58) Field of Classification Search
CPC .................................................... C07D 207/09
USPC ...................................................... 548/537
See application file for complete search history.

(56) References Cited

FOREIGN PATENT DOCUMENTS

WO    2010/121918    10/2010

OTHER PUBLICATIONS

March's Advanced Organic Chemistry, 5th ed., (2001), Ch. 19 provided.*

Hardegger et al., Angewandte Chemie International Edition 50(1):314-318 ( 2011).
International Search Report for PCT/EP2012/072078 dated Dec. 19, 2012.

* cited by examiner

*Primary Examiner* — Robert Havlin

(57) ABSTRACT

The present invention relates in part to a process for the preparation of a proline derivative of formula I

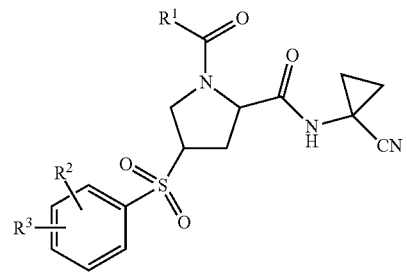

wherein,
$R^1$ is $C_{1-7}$-alkyl or

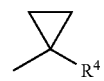

wherein $R^4$ is selected from the group consisting of $C_{1-7}$-alkyl, halogen-$C_{1-7}$-alkyl and phenyl optionally substituted by halogen;
$R^2$ is halogen or halogen-$C_{1-7}$-alkyl; and
$R^3$ is selected from the group consisting of hydrogen, halogen, halogen-$C_{1-7}$-alkyl, $C_{1-7}$-alkoxy, halogen-$C_{1-7}$-alkoxy and a 5- or 6-membered heterocyclic ring containing one or two nitrogen atoms, said ring being optionally substituted by $C_{1-7}$-alkyl or halogen.
The proline derivatives of the formula I are preferential inhibitors of the cysteine protease Cathepsin S and are therefore useful to treat metabolic diseases like diabetes, atherosclerosis, abdominal aortic aneurysm, peripheral arterial disease and diabetic nephropathy.

26 Claims, No Drawings

PROCESS FOR THE PREPARATION OF PROLINE DERIVATIVES

PRIORITY TO RELATED APPLICATIONS

This application claims the benefit of European Patent Application No. 11188728.7, filed Nov. 11, 2011, which is hereby incorporated by reference in its entirety.

SUMMARY OF THE INVENTION

The invention relates to a process for the preparation of a proline derivative of formula I,

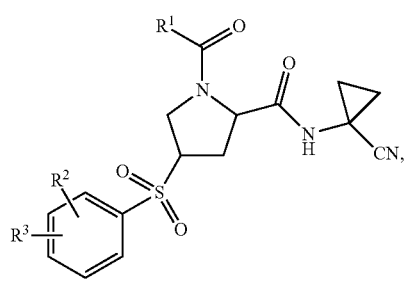

I wherein,
$R^1$ is $C_{1-7}$-alkyl or

wherein $R^4$ is selected from the group consisting of $C_{1-7}$-alkyl, halogen-$C_{1-7}$-alkyl and phenyl optionally substituted by halogen;
$R^2$ is halogen or halogen-$C_{1-7}$-alkyl; and
$R^3$ is selected from the group consisting of hydrogen, halogen, halogen-$C_{1-7}$-alkyl, $C_{1-7}$-alkoxy, halogen-$C_{1-7}$-alkoxy and a 5- or 6-membered heterocyclic ring containing one or two nitrogen atoms, said ring being optionally substituted by $C_{1-7}$-alkyl or halogen.

The proline derivatives of the formula I are preferential inhibitors of the cysteine protease Cathepsin S and are therefore useful to treat metabolic diseases like diabetes, atherosclerosis, abdominal aortic aneurysm, peripheral arterial disease and diabetic nephropathy (PCT Publ. WO 2010/121918).

An object of the present invention is to provide a scalable process for the manufacture of the compounds of formula I.

The object could be achieved with the process of the present invention which comprises the steps of
a) transforming an alcohol of formula II

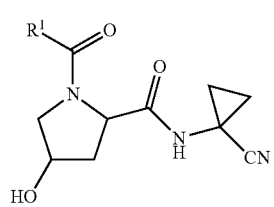

II wherein $R^1$ has the meaning as above into the sulfonate of the formula III

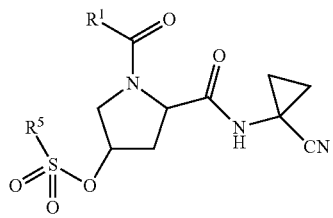

III wherein $R^1$ has the meaning as above and $R^5$ is selected from the group consisting of $C_{1-7}$-alkyl, halogen-$C_{1-7}$-alkyl and phenyl optionally substituted by $C_{1-7}$-alkyl, nitro or bromo;
b) reacting the sulfonate of formula III with a thio compound of formula IV

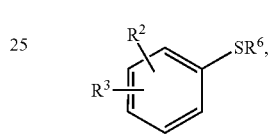

IV wherein $R^2$ and $R^3$ are as outlined above and $R^6$ is hydrogen or a protecting group, to form the thioether of the formula V

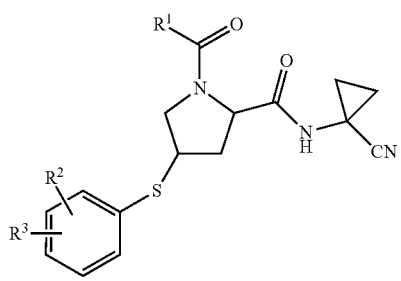

V wherein $R^1$, $R^2$ and $R^3$ are as outlined above and
c) oxidizing the thioether of formula V to form the proline derivative of formula I, wherein $R^1$, $R^2$ and $R^3$ are as outlined above.

The present invention also relates to an alcohol of formula II,

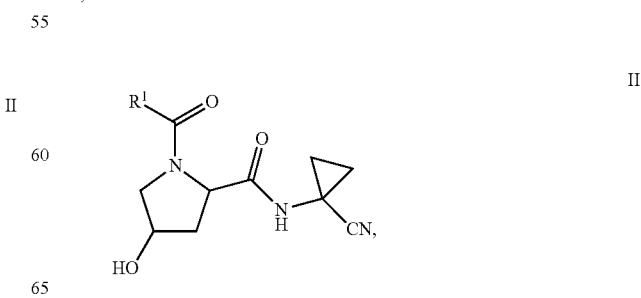

II wherein $R^1$ is as above.

The present invention further relates to a sulfonate of formula III

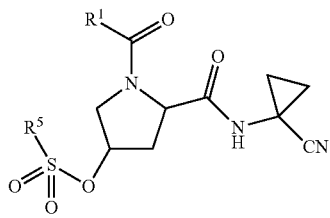

wherein $R^1$ is $C_{1-7}$-alkyl or

wherein $R^4$ is selected from the group consisting of $C_{1-7}$-alkyl, halogen-$C_{1-7}$-alkyl and phenyl which is optionally substituted by halogen and $R^5$ is selected from the group consisting of $C_{1-7}$-alkyl, halogen-$C_{1-7}$-alkyl and phenyl which is optionally substituted by $C_{1-7}$-alkyl, nitro or bromo.

A yet further embodiment of the present invention is a thioester of formula V

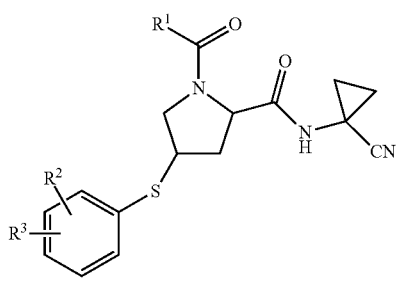

wherein
$R^1$ is $C_{1-7}$-alkyl or

wherein $R^4$ is selected from the group consisting of $C_{1-7}$-alkyl, halogen-$C_{1-7}$-alkyl and phenyl which is optionally substituted by halogen;

$R^2$ is selected from halogen or halogen-$C_{1-7}$-alkyl; and $R^3$ is selected from the group consisting of hydrogen, halogen, halogen-$C_{1-7}$-alkyl, $C_{1-7}$-alkoxy, halogen-$C_{1-7}$-alkoxy and a 5- or 6-membered heterocyclic ring containing one or two nitrogen atoms, said ring being optionally substituted by $C_{1-7}$-alkyl or halogen.

DETAILED DESCRIPTION OF THE INVENTION

The following definitions are set forth to illustrate and define the meaning and scope of the various terms used to describe the invention herein.

The term "$C_{1-7}$-alkyl", alone or in combination with other groups, refers to a branched or straight-chain monovalent saturated aliphatic hydrocarbon radical of one to seven carbon atoms, particularly one to four carbon atoms. This term is further exemplified by radicals such as methyl, ethyl, n-propyl, isopropyl, n-butyl, s-butyl, t-butyl, pentyl, hexyl or heptyl and its isomers.

The term "$C_{1-9}$-alkyl", alone or in combination with other groups, refers to a branched or straight-chain monovalent saturated aliphatic hydrocarbon radical of one to nine carbon atoms, such as methyl, ethyl, n-propyl, isopropyl, n-butyl, s-butyl, t-butyl, pentyl, cyclopentyl, hexyl, cyclohexyl, heptyl, octyl, nonyl and its isomers.

The term "halogen-$C_{1-7}$-alkyl" refers to a halogen substituted $C_{1-7}$-alkyl radical wherein halogen has the meaning as outlined below. Particular "halogen-$C_{1-7}$-alkyl" radicals are the fluorinated $C_{1-7}$-alkyl radicals such as $CF_3$, $CH_2CF_3$, $CH(CF_3)_2$, $CH(CH_3)(CF_3)$, $C_4F_9$, but more particular $CF_3$.

The term "$C_{1-7}$-alkoxy" refers to a branched or straight-chain monovalent saturated aliphatic hydrocarbon radical of one to seven carbon atoms, preferably 1 to 4 carbon atoms attached to an oxygen atom. Examples of "alkoxy" are methoxy, ethoxy, propoxy, isopropoxy, butoxy, isobutoxy, pentoxy, hexyloxy or heptoxy. Particularly used are the alkoxy groups specifically exemplified herein.

The term "mono- or di-($C_{1-7}$-alkyl)-amino", alone or in combination with other groups, refers to one or two branched or straight-chain monovalent saturated aliphatic hydrocarbon radicals of one to seven carbon atoms, preferably 1 to 4 carbon atoms, attached to a nitrogen atom. Optionally, in case of "di-($C_{1-7}$-alkyl)-amino", the two $C_{1-7}$-alkyl radicals can be connected to form a saturated heterocycle containing a nitrogen atom. Examples of "mono- or di-($C_{1-7}$-alkyl)-amino" are methylamino, dimethylamino, ethylamino, diethylamino, pyrrolidinyl, ethylmethylamino, ethylpropylamino or piperidinyl.

The term "halogen-$C_{1-7}$-alkoxy" refers to a halogen substituted $C_{1-7}$-alkoxy radical wherein halogen has the meaning as outlined below. Particular "halogen-$C_{1-7}$-alkoxy" radicals are the fluorinated $C_{1-7}$-alkoxy radicals such as $OCF_3$, $OCH_2CF_3$, $OCH(CF_3)_2$, $OCH(CH_3)(CF_3)$, $OC_4F_9$, but more particular $OCH_2CF_3$ or $OCH(CH_3)(CF_3)$.

The term "5- or 6-membered heterocyclic ring containing one or two nitrogen atoms" relates to an optionally substituted 5- or 6-membered heteroaryl radical containing one or two nitrogen atoms selected from pyridyl, pyridazinyl, pyrimidinyl, pyrazinyl, pyrrolyl, pyrazolyl or imidazolyl, more particularly to pyridinyl or pyrazolyl. A suitable substituent is the $C_{1-7}$-alkyl group, whereby the methyl group is particularly used or is a halogen atom, whereby chlorine is particularly used.

The term "aryl" refers to a phenyl radical that is optionally attached to one to three substituents selected from $C_{1-7}$-alkyl, $C_{1-7}$-alkoxy and mono- or di-($C_{1-7}$-alkyl)-amino.

The term "halogen" refers to a fluorine, chlorine, bromine or iodine atom.

The present invention relates in part to a process for the preparation of a proline derivative of formula I

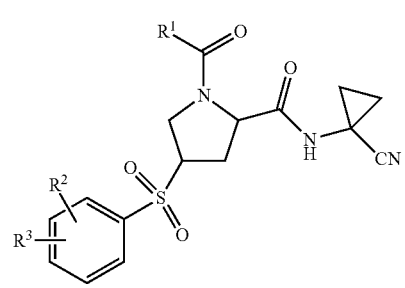

wherein,

R¹ is $C_{1-7}$-alkyl or

wherein R⁴ is selected from the group consisting of $C_{1-7}$-alkyl, halogen-$C_{1-7}$-alkyl and phenyl optionally substituted by halogen;

R² is halogen or halogen-$C_{1-7}$-alkyl; and

R³ is selected from the group consisting of hydrogen, halogen, halogen-$C_{1-7}$-alkyl, $C_{1-7}$-alkoxy, halogen-$C_{1-7}$-alkoxy and a 5- or 6-membered heterocyclic ring containing one or two nitrogen atoms, said ring being optionally substituted by $C_{1-7}$-alkyl or halogen;

comprising the steps of a) transforming an alcohol of formula II

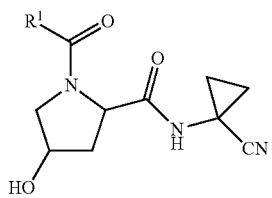

II wherein R¹ has the meaning as above into the sulfonate of the formula III

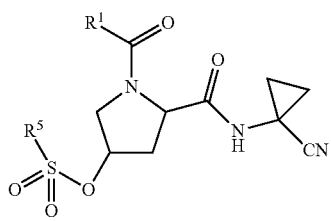

III wherein R¹ has the meaning as above and R⁵ is selected from the group consisting of $C_{1-7}$-alkyl, halogen-$C_{1-7}$-alkyl and phenyl optionally substituted by $C_{1-7}$-alkyl, nitro or bromo b) reacting the sulfonate of formula III with a thio compound of formula IV

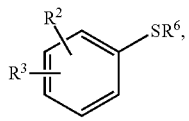

IV wherein R² and R³ are as outlined above and R⁶ is hydrogen or a protecting group, to form the thioether of the formula V

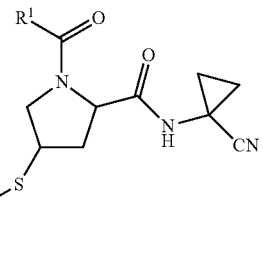

V wherein R¹, R² and R³ are as outlined above and c) oxidizing the thioether of formula V to form the proline derivative of formula I wherein R¹, R² and R³ are as outlined above.

In an embodiment of the present invention, R¹ is $C_{1-7}$-alkyl or

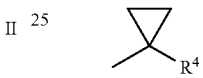

wherein R⁴ is selected from the group consisting of $C_{1-7}$-alkyl, halogen-$C_{1-7}$-alkyl and phenyl optionally substituted by halogen.

In an embodiment of the present invention, R³ is halogen-$C_{1-7}$-alkoxy or a 5- or 6-membered heterocyclic ring containing one or two nitrogen atoms, said ring being optionally substituted by $C_{1-7}$-alkyl or halogen.

In an embodiment of the present invention, the residue of the formula

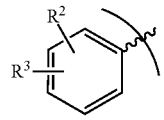

is of the formula

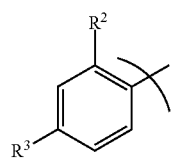

wherein R² and R³ are as above.

Formation of the Alcohol of Formula II:

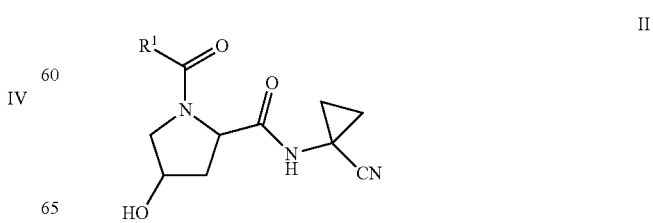

II

The alcohol of formula II
wherein $R^1$ has the meaning as above is accessible either by
a1) reacting a hydroxy proline ester of formula VI

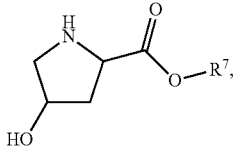

VI wherein $R^7$ is $C_{1-7}$-alkyl,
with a carbonyl compound of formula VII, $R^1COY$ VII, wherein $R^1$ is as above and Y is halogen or OH, to form a carbonyl proline ester of formula IX,

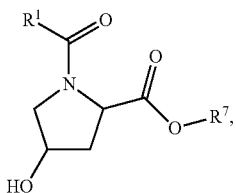

IX wherein $R^1$ and $R^7$ are as above;
b1) transforming said ester of formula IX into a sulfonate of formula X,

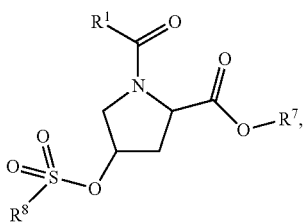

X wherein $R^1$ and $R^7$ are as above and $R^8$ is $C_{1-7}$-alkyl optionally substituted by halogen or phenyl optionally substituted by $C_{1-7}$-alkyl, nitro or bromo and
c1) converting the sulfonate of formula X in the presence of an amino cyclopropane
carbonitrile of formula XI,

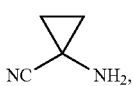

XI into the alcohol of formula II
or by
a2) transforming the sulfonate salt of the formula XII,

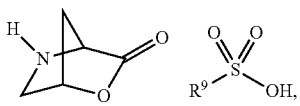

XII wherein $R^9$ is $C_{1-7}$-alkyl or phenyl optionally substituted by $C_{1-7}$-alkyl, into the amide of formula XIII,

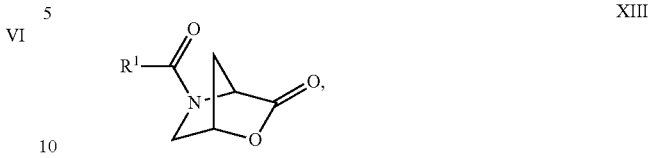

XIII wherein $R^1$ is as above, and subsequently
b2) converting the amide of formula XIII in the presence of the aminocyclopropane carbonitrile of formula XI,

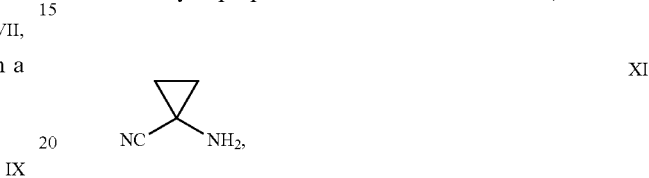

XI into the alcohol of formula II.

In a particular embodiment the alcohol of formula II obtained by the process steps a1) to c1) or a2) to b2) as described above is a chiral isomer of the formula

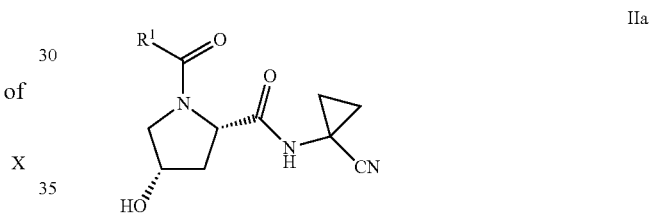

IIa wherein $R^1$ has the meaning as above.
Step a1):
Step a1) requires the reaction of the hydroxy proline ester of formula VI with a carbonyl compound of formula VII to form a carbonyl proline ester of formula IX.

This reaction can follow principles known to the skilled in the art for the formation of amides.

The carbonyl compound of formula VII can be a carbonyl chloride or a carboxylic acid.

The coupling with carboxylic acids as a rule makes use of the common coupling agents for amide bond formation, e.g. summarized in Chemical Reviews, volume 111 (2011), pages 6557 to 6602, such as DCC or DIC.

In a particular embodiment carbonyl chlorides are used which as a rule are prepared in situ by converting the respective carboxylic acid with a common halogenating agent like e.g. oxalylchloride or thionylchloride.

In a particular embodiment of the present invention the hydroxyproline ester of formula VI is the commercially available hydroxyproline methylester hydrochloride.

The reaction as a rule is performed in an inert organic solvent such as dichloromethane, tetrahydrofuran or toluene at temperatures of from −10° C. to 25° C.

Suitably a tertiary amine like triethylamine or diisopropylethylamine is present.

The carbonyl proline ester of formula IX can either be isolated using methods known to the skilled in the art or advantageously kept in solution and transferred to the following reaction step b1).

Step b1):

Step b1) requires the formation of the sulfonate of formula X.

A common sulfonating agent like methanesulfonyl chloride, benzene sulfonyl chloride or p-toluene sulfonyl chloride can as a rule be used.

Accordingly $R^8$ particularly is selected from the group consisting of methyl, phenyl and p-tolyl. In a particular embodiment, $R^8$ is methyl.

The reaction advantageously takes place in the reaction environment of the former step applying reaction temperatures of from −10° C. to 40° C.

The sulfonate of formula X can be isolated using methods known to the skilled in the art such as by extraction from the reaction mixture using a suitable solvent like dichloromethane and by a subsequent crystallization for instance in isobutyl acetate.

Step c1):

Step c1) requires the conversion of the sulfonate of formula X in the presence of aminocyclopropane carbonitrile of the formula XI into the alcohol of formula II.

The reaction encompasses an initial hydrolysis of the ester function suitably with an inorganic aqueous base such as with an aqueous alkali hydroxide like sodium hydroxide, potassium hydroxide or lithium hydroxide at temperatures of from 0° C. to 30° C., followed by intermediary formation of a lactone.

The aminocyclopropane carbonitrile of formula XI can be reacted as free base or as a suitable salt, particularly the hydrochloride salt. The most suitable form is the hydrochloride salt.

The lactone aminolysis using an aminocyclopropane carbonitrile salt, such as the hydrochloride salt, is accelerated by addition of at least stoichiometric amounts of an alkali alkyl- or arylcarboxylate salt $MR^{10}COO$, wherein M is selected from the group consisting of Li, Na, K and Cs, particularly Na, and $R^{10}=C_{1-9}$-alkyl or aryl. In particular, sodium 2-ethylhexanoate can be used to promote the reaction.

Alternatively, the lactone aminolysis using an aminocyclopropane carbonitrile salt, such as the hydrochloride salt, is accelerated by addition of substoichiometric amounts of an alkali alkyl- or arylcarboxylate salt $MR^{10}COO$, wherein M and $R^{10}$ are as defined above, particularly sodium 2-ethylhexanoate, in combination with the addition of stoichiometric amounts of a suitable base, such as triethylamine.

In case of using an aminocyclopropane carbonitrile as free base, the lactone aminolysis is accelerated by addition of stoichiometric or substoichiometric amounts of an alkali alkyl- or arylcarboxylate salt $MR^{10}COO$, wherein M and $R^{10}$ are as defined above, particularly sodium 2-ethylhexanoate, or by addition of stoichiometric or substoichiometric amounts of an alkyl- or arylcarboxylic acid $R^{10}COOH$, wherein $R^{10}$ is as defined above, particularly 2-ethylhexanoic acid.

An organic solvent such as tetrahydrofuran can be added, the reaction is performed at temperatures of from 40° C. to 130° C., particularly from 50° C. to 70° C.

In an embodiment, step c1) is performed in the presence of a carboxylate salt $NaR^{10}COO$, wherein $R^{10}$ is $C_{1-9}$-alkyl or aryl, in a solvent at temperatures between 40° C. and 130° C. Product separation from the reaction mixture can follow procedures known to the skilled in the art such as by extraction with a suitable solvent like ethyl acetate and a subsequent crystallization of the resulting product also with a suitable organic solvent or mixtures thereof like ethylacetate/heptane.

Alternatively the alcohol of formula II can be synthesized as follows:

Step a2)

Step a2) requires the transformation of a sulfonate salt of the formula XII into the amide of formula XIII.

Suitable sulfonate salts of formula XII is either the methane sulfonate salt ($R^9$=methyl) or the p-toluene sulfonate salt ($R^9$=p-tolyl).

These sulfonate salts can be synthesized by methods known in the literature, e.g. reported in Journal of Organic Chemistry, volume 71, pages 7133 to 7145.

The formation of the amide can follow principles known to the skilled in the art and as described above in step a1).

Product separation from the reaction mixture can follow procedures known to the skilled in the art such as by extraction with a suitable solvent like dichloromethane and a subsequent crystallization of the resulting product also with a suitable organic solvent or mixtures thereof like ethylacetate/heptane.

Step b2)

Step b2) requires the conversion of the amide of formula XIII in the presence of aminocyclopropane carbonitrile of the formula XI into the alcohol of formula II.

The aminocyclopropane carbonitrile of formula XI can be reacted as free base or as a suitable salt, particularly the hydrochloride salt. The most suitable form is the hydrochloride salt.

The lactone aminolysis using an aminocyclopropane carbonitrile salt, such as the hydrochloride salt, is accelerated by addition of at least stoichiometric amounts of an alkali alkyl- or arylcarboxylate salt $MR^{10}COO$, wherein M is selected from the group consisting of Li, Na, K and Cs, particularly Na, and $R^{10}$ is $C_{1-9}$-alkyl or aryl. In particular, sodium 2-ethylhexanoate can be used to promote the reaction.

Alternatively, the lactone aminolysis using an aminocyclopropane carbonitrile salt, such as the hydrochloride salt, is accelerated by addition of substoichiometric amounts of an alkali alkyl- or arylcarboxylate salt $MR^{10}COO$, wherein M and $R^{10}$ are as defined above, particularly sodium 2-ethylhexanoate, in combination with the addition of stoichiometric amounts of a suitable base, such as triethylamine.

In case of using an aminocyclopropane carbonitrile as free base, the lactone aminolysis is accelerated by addition of stoichiometric or substoichiometric amounts of an alkali alkyl- or arylcarboxylate salt $MR^{10}COO$, wherein M and $R^{10}$ are as defined above, particularly sodium 2-ethylhexanoate, or by addition of stoichiometric or substoichiometric amounts of an alkyl- or arylcarboxylic acid $R^{10}COOH$, wherein $R^{10}$ is as defined above, particularly 2-ethylhexanoic acid.

The reaction usually is performed in polar solvents such as tetrahydrofuran, dichloromethane, water, or mixtures thereof, or under neat conditions, at temperatures of from 40° C. to 130° C., particularly from 50° C. to 70° C.

In an embodiment, step b2) is performed in the presence of an alkali alkyl- or arylcarboxylate salt $MR^{10}COO$, wherein M is selected from the group consisting of Li, Na, K and Cs and $R^{10}$ is $C_{1-9}$-alkyl or aryl, in a solvent at a temperature between 40° C. and 130° C. In particular, sodium 2-ethylhexanoate can be used to promote the reaction.

Product separation from the reaction mixture can follow procedures known to the skilled in the art such as by extraction with a suitable solvent like ethyl acetate and a subsequent crystallization of the resulting product also with a suitable organic solvent or mixtures thereof like ethylacetate/heptane.

The alcohol of formula II

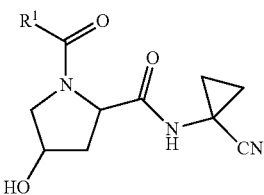

wherein $R^1$ is as above is not known in the art and thus is a particular embodiment of the present invention.

In a further particular embodiment $R^1$ has the meaning of

wherein $R^4$ is selected from the group consisting of $C_{1-7}$-alkyl, halogen-$C_{1-7}$-alkyl and phenyl optionally substituted by halogen.

More particularly $R^4$ is methyl or trifluoromethyl.

In a further particular embodiment the alcohol of formula II is a chiral isomer of the formula

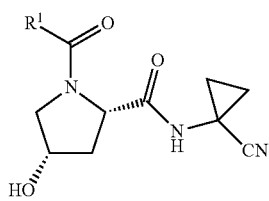

wherein $R^1$ has the meaning as above.

Formation of the Thio Compound of Formula IV:

Thio Compound of Formula IV with $R^6$=H

The thio compound of formula IV

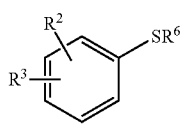

wherein $R^2$ and $R^3$ are as above and $R^6$ is hydrogen can be prepared by a3) deprotecting a compound of formula XX

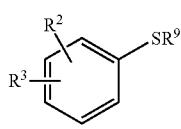

wherein $R^2$ and $R^3$ are as above and $R^9$ is a tertiary alkyl group of the formula

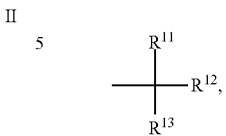

wherein $R^{11}$, $R^{12}$ and $R^{13}$ independently of each other are $C_{1-7}$-alkyl,
with an acid;
or by
b3) deprotecting a compound of formula XX,

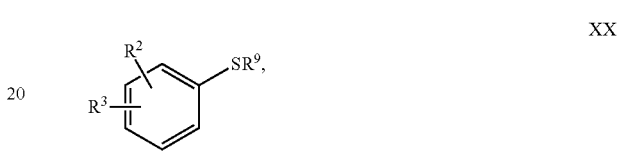

wherein $R^2$ and $R^3$ are as above and $R^9$ is trityl, with an acid in the presence of a reductive agent;
c3) lithiating a halogenated compound of formula XXI,

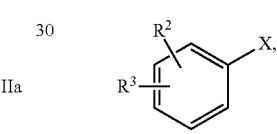

wherein $R^2$ and $R^3$ are as above and X is a halogen atom, and subsequently treating with sulfur;
or by
d3) reacting a halogenated compound of formula XXI,

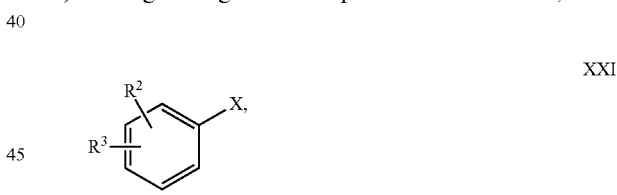

wherein $R^2$ and $R^3$ are as above and X is a halogen atom, with a Grignard reagent and subsequently treating with sulfur.

Step a3)

Process variant a3) requires deprotecting a compound of formula XX, wherein $R^9$ is a tertiary alkyl group, with an acid. $R^9$ particularly has the formula

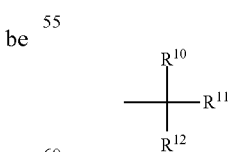

wherein $R^{10}$, $R^{11}$ and $R^{12}$ independently of each other stand for $C_{1-7}$-alkyl and more particularly for $C_{1-4}$-alkyl. Even more particularly $R^9$ stands for tert-butyl.

In an embodiment of the invention, the acid used in the reaction step a3) is an aqueous mineral acid or an organic acid.-

Compounds of formula XX are either commercially available or accessible by methods readily available to the skilled in the art.

Compounds of formula XX with $R^9$=tert-butyl can be prepared by converting the respective fluoro precursor compound with 2-methyl-2-propane thiol in the presence of an alkali alkoxide.

Suitable acids can be selected from aqueous mineral acids like aqueous hydrochloric acid or aqueous sulfuric acid or by organic acids like trifluoro acetic acid.

An organic solvent like dichloromethane may be present when an organic acid is used.

The reaction conditions and the isolation of the thio compound of the formula IV depend on the acid used but its adaptation can follow methods known to the skilled in the art.

Step b3)

Process variant b3) requires deprotecting a compound of formula XX, wherein $R^9$ is trityl, with trifluoro acetic acid in the presence of a reductive agent.

A suitable reductive agent is triethylsilane.

An organic solvent like dichloromethane may be present.

The reaction conditions and the isolation of the thio compound of the formula IV can follow methods known to the skilled in the art.

Step c3)

Process variant c3) involves lithiating a halogenated compound of formula XXI and a subsequent treatment with sulfur.

In a particular embodiment X is bromo.

Suitable lithiating agents can be selected from commercially available lithiating agents like butyl lithium.

The lithiation as a rule takes place in the presence of an organic solvent such as in toluene at temperatures between −80° C. and −20° C.

In an embodiment, the reaction step in c3) is performed with butyl lithium as a lithiating agent in an organic solvent at temperatures between −80° C. and −40° C.

In an embodiment, the reaction with sulfur in step c3) is performed with in an organic solvent at temperatures between −80° C. and −40° C.

A chelating agent, such as diethyl ether or di-n-propyl ether is suitably present as well.

Subsequent sulfur treatment can happen at temperatures between −80° C. and −40° C. usually in the same reaction environment as for the lithiation.

The isolation of the thio compound of the formula IV can follow methods known to the skilled in the art.

Step d3)

Process variant d3) involves reacting a halogenated compound of formula XXI with a Grignard reagent and a subsequent treatment with sulfur.

In a particular embodiment X is bromo.

Suitable Grignard agents can be selected from commercially available Grignard agents like isopropyl magnesium chloride or isopropyl magnesium chloride/lithium chloride in tetrahydrofuran.

The Grignard reaction as a rule takes place in the presence of the organic solvent the Grignard reagent is commercially available such as in tetrahydrofuran.

The reaction temperature is suitably held between 0° C. and 40° C., particularly at about room temperature.

In an embodiment, the reaction in step d3) is performed with a Grignard reagent which is isopropyl magnesium chloride or isopropyl magnesium chloride/lithium chloride in an organic solvent at temperatures between 0° C. and 40° C.

Subsequent sulfur treatment can happen at temperatures between −20° C. and 20° C. usually in the same reaction environment as for the Grignard reaction. The isolation of the thio compound of the formula IV can follow methods known to the skilled in the art.

Thio Compound of Formula IV with $R^6$=Protecting Group

Suitable protecting groups can be selected from the group consisting of 2-carbamoyl-ethyl, $C_{1-7}$-alkoxycarbonyl-ethyl-, or mono and di-$C_{1-7}$-alkyl aminocarbonyl-ethyl.

$R^6$=2-carbamoyl-ethyl was found to be particularly suitable.

These compounds can be prepared following the scheme below. X is a halogen atom, particularly bromine, $R^2$ and $R^3$ are as above.

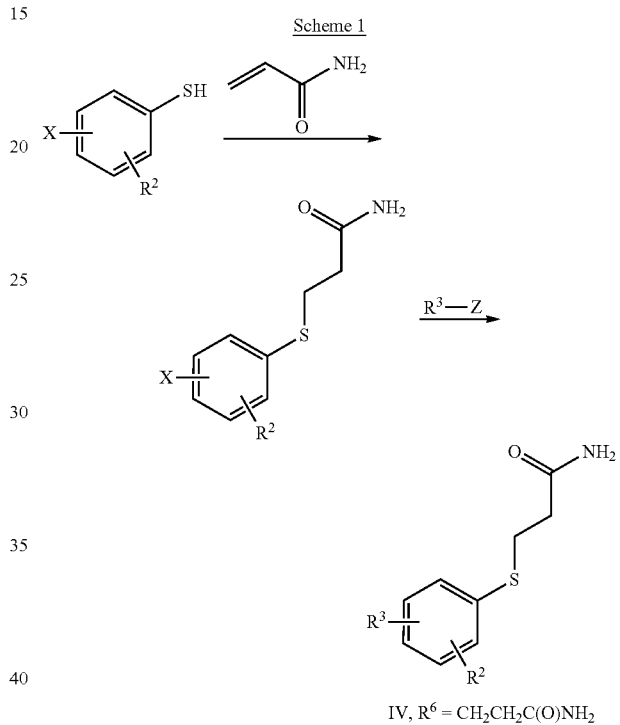

IV, $R^6$ = $CH_2CH_2C(O)NH_2$

The 2-carbamoyl-ethyl protecting group can be installed by reacting the corresponding thiophenol with acrylamide in the presence of a catalytic (or stoichiometric) amount of a suitable base, e.g. sodium tetraborate, in a suitable polar solvent, such as methanol or water or mixtures thereof. For other, substituted propionamide or -ester protecting groups the reacting acryl amide is replaced accordingly. The resulting protected thiophenol can then be manipulated using methods known to the person skilled in the art. As example, a bromine atom can be replaced by a 5- or 6-membered heterocyclic ring $R^3$ as defined above by reacting it with a suitable reactant $R^3$—Z, wherein Z=$B(OH)_2$, $B(OMe)_2$, $B(OEt)_2$, $B(OiPr)_2$, 4,4,5,5-tetramethyl-[1,3,2]-dioxaboryl)-, $Sn(n-Bu)_3$, MgX, ZnX or $Si(OEt)_3$, particularly $B(OH)_2$ or 4,4,5,5-tetramethyl-[1,3,2]-dioxaboryl)-. In the particular cases, the reaction is performed in the presence of a catalytic amount of a suitable transition metal complex, e.g. [1,1'-bis(diphenylphosphino)ferrocene]dichloropalladium(II) or tetrakis(triphenylphoshin)palladium(0), stoichiometric amounts of a suitable base, e.g. potassium carbonate, sodium carbonate or potassium phosphate, in a suitable solvent, such as for example dimethylformamide, dimethylacetamide, toluene, tetrahydrofuran, tert-butanol, N-methylpyrrolidone or dioxane, optionally and preferably as mixtures thereof with water, at elevated temperatures from 40° C. to 140° C., particularly from 50° C. to 70° C. Optionally, the reactants $R^3$—Z as described above, particularly Z=4,4,5,5-tetramethyl-[1,3,2]-dioxaboryl)-, can be formed in situ starting from the appropriate $R^3$—X, wherein X has the meaning of a halogen atom, particularly bromine or iodine, and reacting it with 4,4,4',4',5,5,5',5'-octamethyl-2,2'-bi(1,3,2-dioxaborolane) in the presence of an appropriate base, e.g. potassium acetate or sodium acetate, and a catalytic amount of a suitable palladium complex, such as [1,1'-bis(diphenylphosphino)ferrocene]dichloropalladium(II), in a suitable solvent e.g. dimethylformamide, at temperatures of 60° C. to 120° C., particularly 70° C. to 90° C., and reacted further in one pot with the protected halothiophenol, particularly using similar, more particularly the same solvent and palladium complex.

Step a)

Step a) requires the transformation of an alcohol of the formula II into the sulfonate of the formula III.

In a particular embodiment a chiral isomer of the alcohol of the formula II having the formula

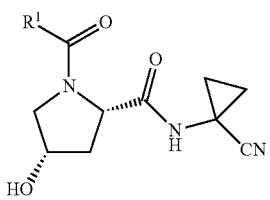

IIa wherein $R^1$ has the meaning as above is used.

The sulfonation follows methods known to the skilled in the art applying common commercially available sulfonating agents. Particular sulfonating agent is benzenesulfonyl chloride or methanesulfonyl chloride.

As a rule a tertiary amine such as triethylamine is present. The reaction may be accelerated by addition of a suitable Lewis base, e.g. 4-(dimethylamino)pyridine.

The reaction as a rule takes place in an organic solvent such as in tetrahydrofuran at temperatures between −10° C. and 40° C.

The isolation of the sulfonate of formula III can follow methods known to the skilled in the art.

The sulfonate of formula III

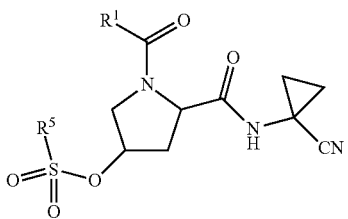

III wherein $R^1$ has the meaning as above and $R^5$ is $C_{1-7}$-alkyl, halogen-$C_{1-7}$-alkyl or phenyl which is optionally substituted by $C_{1-7}$-alkyl, nitro or bromo is not known in the art and thus is a particular embodiment of the present invention.

In a further particular embodiment $R^1$ has the meaning of

wherein $R^4$ is selected from the group consisting of $C_{1-7}$-alkyl, halogen-$C_{1-7}$-alkyl and phenyl which is optionally substituted by halogen and $R^5$ is $C_{1-7}$-alkyl or phenyl optionally substituted by $C_{1-7}$-alkyl.

More particularly $R^4$ is methyl or trifluoromethyl and $R^5$ is methyl or phenyl.

In a further particular embodiment the sulfonate of formula III is a chiral isomer of the formula

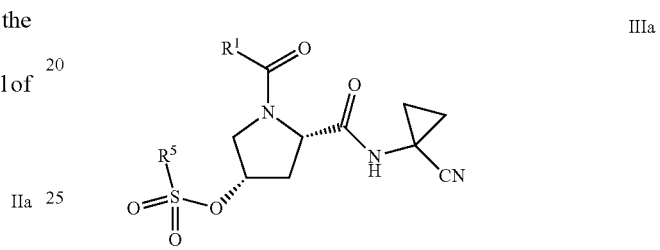

IIIa wherein $R^1$ and $R^5$ are as above.

Step b

Step b) requires reacting the sulfonate of formula III with a thio compound of formula IV to form the thioether of the formula V.

The reaction is suitably performed in the presence of a base, such as an alkali alcoholate or an alkali carbonate.

More particularly a lithium-, sodium- or potassium tert-butylate is used. An inert organic solvent like tetrahydrofuran or dimethyl acetamide, or mixtures thereof, is suitably present.

The reaction temperature can be selected between 10° C. and 90° C.

The thioether of formula V can be separated from the reaction mixture following procedures known to the skilled in the art such as by extraction with a suitable solvent like ethyl acetate or tert-butyl methyl ether. Further purification may be achieved by crystallization in a suitable solvent like toluene, n-heptane, 2-butanol or mixtures thereof.

The thioether of the formula V

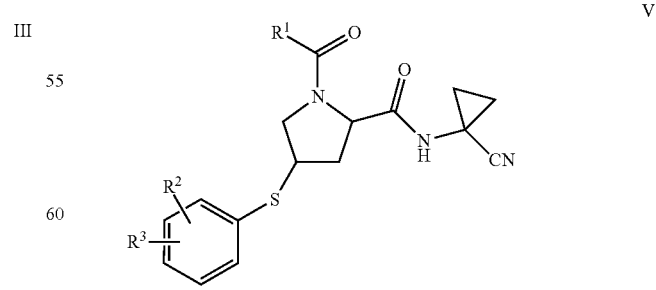

V wherein $R^1$, $R^2$ and $R^3$ are as outlined above is not known in the art and thus is a particular embodiment of the present invention.

In a further particular embodiment
R¹ has the meaning of

wherein R⁴ is selected from the group consisting of $C_{1-7}$-alkyl, halogen-$C_{1-7}$-alkyl and phenyl which is optionally substituted by halogen,
R² is halogen or halogen-$C_{1-7}$-alkyl and
R³ is halogen-$C_{1-7}$-alkoxy or a 5- or 6-membered heterocyclic ring containing one or two nitrogen atoms, said ring being optionally substituted by $C_{1-7}$-alkyl or halogen.

More particularly
R⁴ is methyl trifluoromethyl,
R² is trifluoromethyl or chlorine and
R³ is selected from the group consisting of 2,2,2-trifluoroethoxy, 2-methylpyrid-4-yl, 1-methyl-1H-pyrazol-4-yl and 2,2,2-trifluoro-1-methylethoxy.

In a further particular embodiment the thioether of the formula V is a chiral isomer of the formula

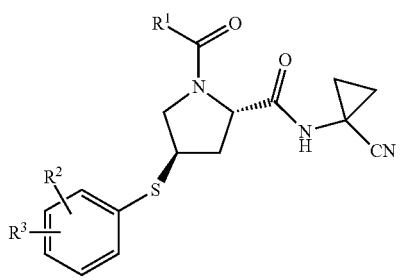

Va even more particular

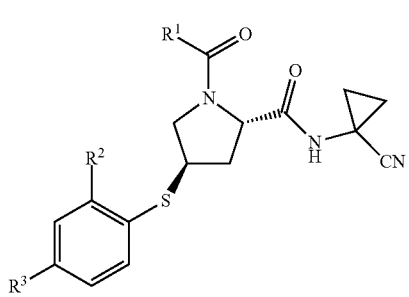

Vb wherein R¹, R² and R³ have the meaning as above.

Step c)

Step c) requires oxidizing the thioether of formula V to form the proline derivative of formula I.

The oxidation reaction can be performed with a commercially available oxidating agent such as with potassium peroxymonosulfate, that is, as example, available as a triple salt in Oxone®, or magnesium monoperoxyphthalate hexahydrate.

A polar organic solvent like methanol or acetonitrile is suitably used. Optionally water or aqueous inorganic acids like sulfuric acid or phosphoric acid may further be added.

The reaction temperature can be selected between 0° C. and 60° C.

The proline derivative of formula I can be separated from the reaction mixture following procedures known to the skilled in the art such as by extraction with a suitable solvent like ethyl acetate. Further purification may be achieved by crystallization in a suitable solvent like acetone, isopropanol, water or mixtures thereof.

In a particular embodiment of the present invention the proline derivatives of the formula I are chiral isomers of the formula

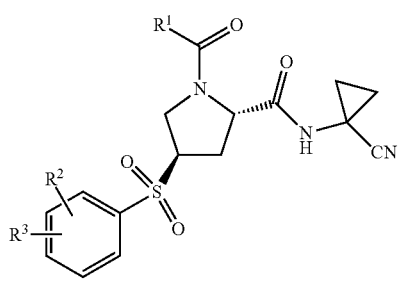

Ia even more particular of formula

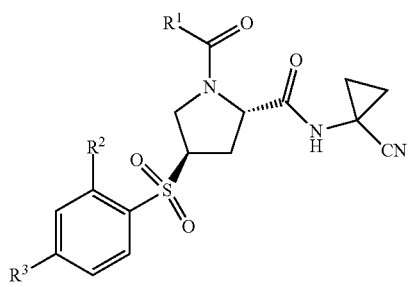

Ib wherein R¹, R² and R³ are as outlined below.
In a further particular embodiment
R¹ has the meaning of

wherein R⁴ is selected from the group consisting of $C_{1-7}$-alkyl, halogen-$C_{1-7}$-alkyl and phenyl optionally substituted by halogen,
R² is halogen or halogen-$C_{1-7}$-alkyl and
R³ is halogen-$C_{1-7}$-alkoxy or a 5- or 6-membered heterocyclic ring containing one or two nitrogen atoms, said ring being optionally substituted by $C_{1-7}$-alkyl or halogen.

More particularly
R⁴ is methyl or trifluoromethyl,
R² is trifluoromethyl or chlorine and
R³ is selected from the group consisting of 2,2,2-trifluoroethoxy, 2-methylpyrid-4-yl, 1-methyl-1H-pyrazol-4-yl and 2,2,2-trifluoro-1-methylethoxy.

EXAMPLES

General Part

All solvents and reagents were obtained from commercial sources and were used as received. The reactions were as a rule followed by TLC (TLC plates F254, Merck) or LC (liquid chromatography) or GC (gas chromatography) analysis. Proton NMR spectra were obtained on Bruker 300, 400 or 600 MHz instruments with chemical shifts (δ in ppm) reported relative to tetramethylsilane as internal standard in the following format: chemical shift in ppm (peak form, coupling constant if applicable, integral). NMR abbreviations are as follows: s, singlet; d, doublet; t, triplet; q, quadruplet; quint, quintuplet; sext, sextuplet; hept, heptuplet; m, multiplet; br, broadened. Purity was analyzed by reverse phase HPLC. HPLC was performed on Agilent 1100 & 1200 equipment. Elemental analyses were performed by Solvias AG (Mattenstrasse, Postfach, CH-4002 Basel, Switzerland). Column chromatography was carried out on silica gel 60 (32-60 mesh, 60 Å) or on prepacked columns (Isolute Flash Si). Mass spectra were recorded on an Agilent 6520 QTOF spectrometer for ESI (electrospray ionization) & APCI (atmospheric pressure chemical ionization), that is achieved simultaneously (multimode), and on an Agilent 5975 instrument for EI (electron ionization) mode, with either positive (pos.) or negative (neg.) charged ion detection. If not otherwise stated, positive charged ions are detected.

Alcohol Formation

A1. Preparation of (2S,4S)-4-hydroxy-1-(1-trifluoromethyl-cyclopropanecarbonyl)-pyrrolidine-2-carboxylic acid (1-cyano-cyclopropyl)-amide a.) (1S,4S)-3-Oxo-2-oxa-5-azonia-bicyclo[2.2.1]heptane methanesulfonate

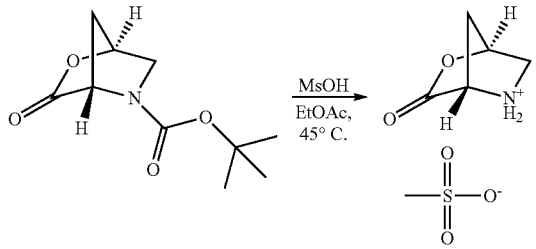

(1S,4S)-3-Oxo-2-oxa-5-aza-bicyclo[2.2.1]heptane-5-carboxylic acid tert-butyl ester (100.0 g, 469 mmol) was dissolved in ethyl acetate (970 mL) and methanesulfonic acid (43.5 mL, 659 mmol) was added at 45° C. The mixture was stirred for 16 h at 45° C. The suspension was cooled to room temperature, filtered, and the precipitate was washed with ethyl acetate (240 mL) and dried in vacuo to yield the title compound as a white crystalline solid (94.2 g, 96%). MS (EI, neg): m/z=113 [cation-H]$^+$, 69 [cation-H—CO$_2$]$^+$, 68 [cation-H—HCO$_2$]$^+$. $^1$H NMR (DMSO-d6, 600 MHz): δ 2.12 (dd, J=1.2 Hz, 12.0 Hz, 1H), 2.33 (s, 3H), 2.59 (d, J=12.0 Hz, 1H), 3.33 and 3.50 (ABX, J$_{AB}$=12.0 Hz, J$_{AX}$=1.9 Hz, J$_{BX}$=0 Hz, each 1H), 4.58 (s, 1H), 5.41 (s, 1H), 9.74 (br s, 2H).

b) (1S,4S)-5-(1-Trifluoromethyl-cyclopropanecarbonyl)-2-oxa-5-aza-bicyclo[2.2.1]heptan-3-one

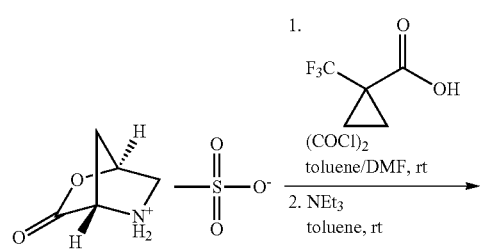

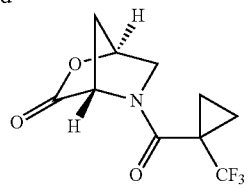

Trifluoromethyl-cyclopropanecarboxylic acid (167.0 g, 1084 mmol) was suspended in toluene (500 mL) and then dimethylformamide (3.6 mL, 47 mmol) was added. The mixture was cooled to 2° C. (ice bath) and a solution of oxalyl chloride (90 mL, 1037 mmol) in toluene (167 mL) was added dropwise (within 25 min). The mixture was then stirred for additional 30 min, followed by 4 h at room temperature. Subsequently, it was cooled to 0° C. again (dry ice/methanol bath) and (1S,4S)-3-oxo-2-oxa-5-azonia-bicyclo[2.2.1]heptane methanesulfonate (200 g, 956 mmol), tetrahydrofuran (330 mL) and triethylamine (500 mL, 3.59 mol) were slowly added, keeping the reaction temperature below 5° C. Especially after addition of 50% of triethylamine, the reaction becomes strongly exothermic and efficient cooling is essential. The mixture was stirred for 20 h at room temperature, before it was poured onto an aqueous citric acid solution (10% in water, 1.6 L) and the phases were separated. The aqueous phase was extracted with ethyl acetate (3×500 mL). The combined organic extracts were washed with brine (500 mL), dried over sodium sulfate, and concentrated in vacuo. The crude product (245 g, brown oil) was dissolved in dichloromethane (330 mL) before ethyl acetate (130 mL) and heptane (660 mL) were added and dichloromethane was carefully distilled off in vacuo. The product started to crystallize. The suspension was cooled to 2° C. (ice bath) and stirred for 1 h, before it was filtered. The precipitate was washed with ethyl acetate/heptane 1:9 (v/v, 300 mL) and dried in vacuo to afford the title compound as a light brown powder (219 g, 92%). $^1$H NMR (CDCl$_3$, 400 MHz): δ 1.17-1.25 (m, 1H), 1.30 (dd, J=5.3 Hz, 8.3 Hz, 1H), 1.37-1.46 (m, 2H), 2.13 and 2.37 (AB, J$_{AB}$=10.7 Hz, each 1H), 3.63 and 3.73 (AB, J$_{AB}$=12.1 Hz, each 1H), 4.99 (s, 1H), 5.21 (s, 1H).

c) (1S,4S)-5-(1-Methyl-cyclopropanecarbonyl)-2-oxa-5-aza-bicyclo[2.2.1]heptan-3-one

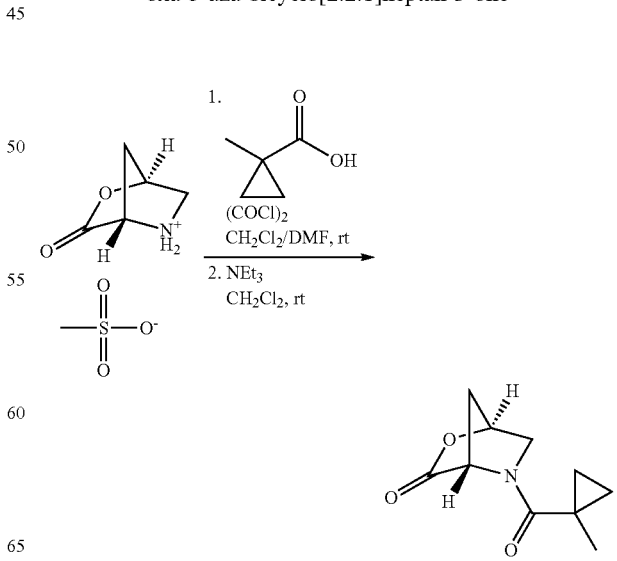

Methyl-cyclopropanecarboxylic acid (56.4 g, 552 mmol) was dissolved in dichloromethane (365 mL) and dimethylformamide (405 μl, 5.2 mmol) was added. The mixture was cooled to 2° C. and oxalyl chloride (70.8 g, 547 mmol) was added dropwise. It was allowed to warm and stirred for 90 min at room temperature. After that, it was added to a suspension of (1S,4S)-3-oxo-2-oxa-5-azonia-bicyclo[2.2.1] heptane methanesulfonate (110 g, 526 mmol) in dichloromethane (400 mL). The resulting suspension was cooled to 2° C. and triethylamine (256 mL, 1.84 mol) was added slowly (exothermic). After stirring for 70 min at room temperature, a solution of citric acid (81.0 g, 421 mmol) in water (550 mL) was added at 2° C. After separation of the phases, the aqueous phase was extracted with dichloromethane (300 mL). The combined organic extracts were washed with water (400 mL) and concentrated in vacuo to a volume of ca. 500 mL. Ethyl acetate (330 mL) was added and the residual dichloromethane was distilled off in vacuo (internal temperature 40° C.). Further ethyl acetate (50 mL) was added, internal temperature was increased to 50° C. and heptane (800 mL) was added slowly. Crystallization started after addition of ca. 300 mL heptane. The suspension was stirred for 12 h at room temperature and filtered. The crystals were washed with cold heptane (400 mL) and dried in vacuo at 40° C. to afford the title compound as colorless crystals (88.45 g, 86%). mp. 101-102° C. MS (ESI & APCI): m/z=196.1 [M+H]$^+$. $^1$H NMR (CDCl$_3$, 600 MHz); δ 0.60-0.67 (m, 2H), 0.87-0.91 (m, 1H), 1.13-1.17 (m, 1H), 1.39 (s, 3H), 2.04 (dd, J=1.2 Hz, 10.9 Hz, 1H), 2.32 (d, J=10.8 Hz, 1H), 3.59 and 3.69 (AB, J$_{AB}$=11.5 Hz, each 1H), 4.97 (s, 1H), 5.18 (s, 1H).

d) (2S,4S)-4-Hydroxy-1-(1-trifluoromethyl-cyclopropanecarbonyl)-pyrrolidine-2-carboxylic acid (1-cyano-cyclopropyl)-amide

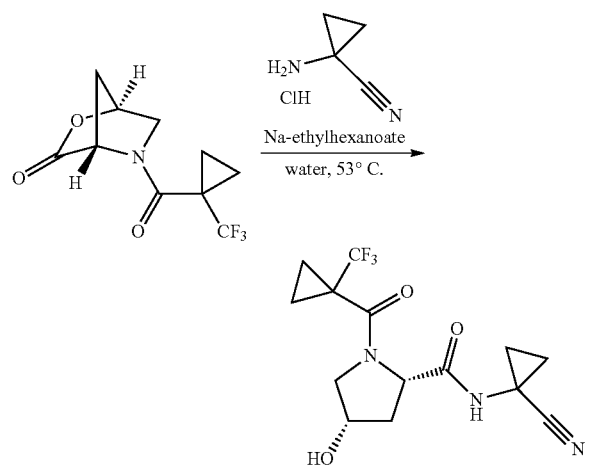

(1S,4S)-5-(1-Trifluoromethyl-cyclopropanecarbonyl)-2-oxa-5-aza-bicyclo[2.2.1]heptan-3-one (220 g, 883 mmol), 1-amino-cyclopropanecarbonitrile hydrochloride (140 g, 1.18 mol) and sodium 2-ethylhexanoate (97%, 230 g, 1.34 mol) were dissolved in water (1.32 L). The mixture was stirred for 20 h at 53° C. After cooling to room temperature, tetrahydrofuran (880 mL) was added and the mixture was acidified by addition of concentrated hydrochloric acid (37% m/m, 47 mL), followed by the addition of sodium chloride (440 g). After extraction with ethyl acetate (1×1.4 L, 3×550 mL), the combined organic extracts were dried over sodium sulfate and concentrated in vacuo. At a volume of ca. 1.5 L, the product started to crystallize upon addition of seed crystals. The volume of the suspension was further reduced to ca. 500 mL and cooled to 2° C. (ice bath). After stirring for 60 min, the crystals were filtered off, washed with ethyl acetate/heptane 1:1 (v/v, 600 mL) and heptane (300 mL), and dried in vacuo to provide the title compound as off-white crystals (255.0 g, 87%). $^1$H NMR (CDCl$_3$, 400 MHz): δ 1.18-1.29 (m, 4H), 1.30-1.42 (m, 2H), 1.50-1.59 (m, 2H), 2.17-2.26 (m, 1H), 2.29 (d, J=14.5 Hz, 1H), 3.73 and 3.96 (ABX, J$_{AB}$=11.8 Hz, J$_{AX}$=4.3 Hz, J$_{BX}$=0 Hz, each 1H), 4.43-4.53 (m, 2H), 4.81 (br d, J=8.3 Hz, 1H), 7.73 (s, 1H).

A2. Preparation of (2S,4S)-4-hydroxy-1-(1-trifluoromethyl-cyclopropanecarbonyl)-pyrrolidine-2-carboxylic acid (1-cyano-cyclopropyl)-amide a) (2S,4R)-4-Methanesulfonyloxy-1-(1-trifluoromethyl-cyclopropanecarbonyl)-pyrrolidine-2-carboxylic acid methyl ester

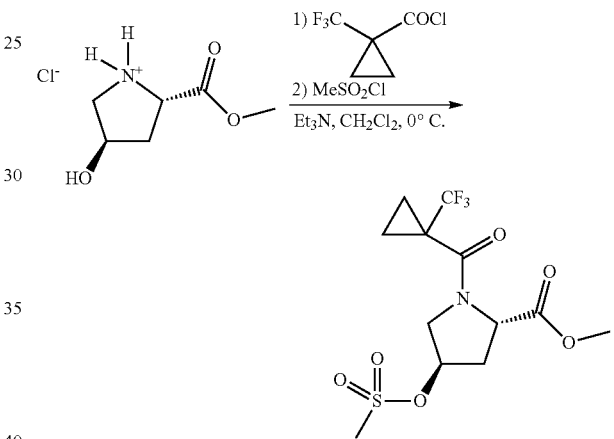

To a stirred suspension of 1-trifluoromethylcyclopropane-1-carboxylic acid (40.4 g, 263 mmol) and DMF (0.4 mL, 5.25 mmol) in dichloromethane (50 mL) was added oxalyl chloride (36.7 g, 289 mmol) under stirring at room temperature over 2 h (vigorous gas evolution!). After additional stirring for 0.5 h (the gas evolution has stopped), the clear acid chloride solution was transferred into an 100 mL addition funnel and added under vigorous stirring at 0° C. over 0.5 h to a suspension of hydroxyproline methyl ester hydrochloride (45.4 g, 250 mmol) and triethylamine (101 g, 1000 mmol) in dichloromethane (950 mL). After additional stirring at 0° C. for 1 h, methanesulfonyl chloride (31.5 g, 275 mmol) was added over 0.5 h, stirring at 0° C. was continued for 0.5 h and the cold suspension was hydrolyzed with 1 M HCl (500 mL, pH=1). After warming to room temperature the organic layer was washed with 5% brine (500 mL) and the two aqueous layers were extracted with dichloromethane (250 mL). The combined organic layers were dried (Na$_2$SO$_4$) and evaporated (35-45° C./≥10 mbar) affording beige, crystalline crude product (91.4 g) which was dissolved in isopropyl acetate (360 mL) at ~70° C. Crystallization, which started upon cooling and seeding, was completed by stirring at room temperature, followed by drop wise addition of heptane (540 mL) and stirring at -20° C. for 4 h. Filtration and washing with cold isopropyl acetate-heptane 2:3 gave after drying (10 mbar/55° C./4 h) the product (83.2 g, 92.6%) as an off-white, crystalline powder, mp. 123-124° C. $[\alpha]_D^{20}=-26.6$ (c 1.0; CHCl$_3$). $^1$H NMR (CDCl$_3$, 400 MHz) δ 1.10-1.42 (m, 4H), 2.18-2.30 (m, 1H), 2.58-2.70 (m, 1H), 3.06 & 3.76 (s, each 3H), 3.90 (dd, J$_1$=12.8 Hz, J$_2$=3.2 Hz, 1H), 4.32 (d, J=12.8 Hz, 1H), 4.68 (t, J=8.3 Hz, 1H), 5.33 (s, 1H). ESI-MS (m/z) [M+H]$^+$ 360 (100).

b) (2S,4S)-4-Hydroxy-1-(1-trifluoromethyl-cyclopropanecarbonyl)-pyrrolidine-2

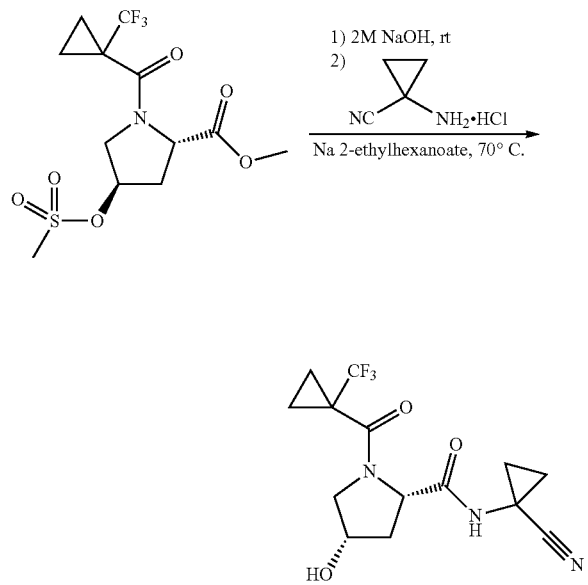

To the (2S,4R)-4-methanesulfonyloxy-1-(1-trifluoromethyl-cyclopropanecarbonyl)-pyrrolidine-2-carboxylic acid methyl ester (71.9 g, 200 mmol) were added under stirring and ice-cooling 2.0 M NaOH (120.0 mL, 240.0 mmol) all at once. The ice bath was removed and the white suspension was stirred at room temperature for 1 h. After neutralization by the addition of 2.0 M HCl (20.0 mL, 40.0 mmol; pH ~7), 1-aminocyclopropanecarbonitrile hydrochloride (23.7 g 200 mmol) and sodium 2-ethylhexanoate (37.7 g, 220 mmol) were added all at once and the biphasic reaction mixture was stirred at 70° C. for 22 h and then cooled to ~35° C. Dichloromethane (100 mL) and NaCl (16 g) were added and stirring was continued until the NaCl was dissolved (~15 min). After acidification with 25% HCl (~12 mL, pH ~1), the reaction mixture was extracted with dichloromethane (3×200 mL) and all three organic layers were washed separately with 5% NaHCO$_3$ (40 mL pH ~8). The combined organic layers were dried (Na$_2$SO$_4$), filtered, and evaporated (35-50° C./≥5 mbar), affording beige, crystalline residue (88.5 g) which was dissolved in isobutyl acetate (500 mL) at ~110° C. Crystallization, which started after seeding and cooling, was completed by stirring at room temperature for 1 h and at −20° C. for 4 h. Filtration and washing with cold isobutyl acetate gave after drying (10 mbar/55° C./4 h) the title product (47.7 g, 72.0%) as an off white, crystalline powder, mp. 156-157° C. $[\alpha]_D^{20}=-68.9$ (c 1.0; CHCl$_3$). $^1$H NMR (CDCl$_3$, 400 MHz) δ 1.15-1.45 (m, 6H), 1.50-1.60 (m, 2H), 2.17-2.29 (m, 2H), 3.72 (dd, J$_1$=11.8 Hz, J$_2$=4.0 Hz, 1H), 3.98 (d, J=11.8 Hz, 1H), 4.40-4.52 (m, 2H), 4.95 (d, J=9.7 Hz, 1H), 7.93 (s, 1H). ESI-MS (m/z) [M+H]$^{+332}$ (56).

A3. Preparation of (2S,4S)-4-hydroxy-1-(1-methyl-cyclopropanecarbonyl)-pyrrolidine-2-carboxylic acid (1-cyano-cyclopropyl)-amide

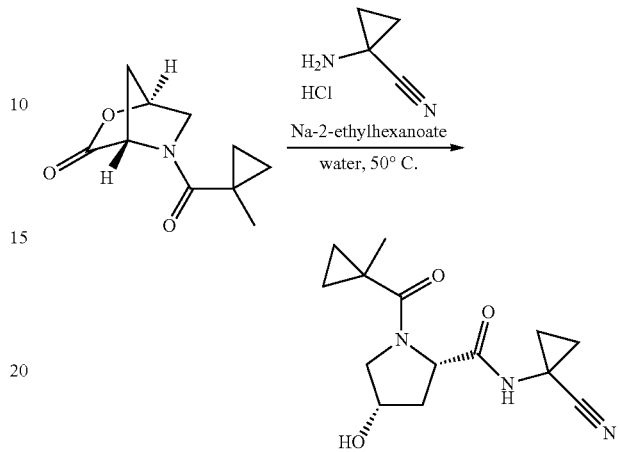

(1S,4S)-5-(1-Methyl-cyclopropanecarbonyl)-2-oxa-5-aza-bicyclo[2.2.1]heptan-3-one (100 g, 512 mmol), 1-aminocyclopropanecarbonitrile hydrochloride (62.0 g, 523 mmol), and sodium 2-ethylhexanoate (97%, 96.5 g, 563 mmol) were dissolved in water (500 mL). The mixture was stirred for 16 h at 50° C. After cooling to room temperature, dichloromethane (500 mL) was added, the mixture was acidified by addition of hydrochloric acid (25% m/m, 13.8 mL, 106 mmol), and sodium chloride (120 g) was added. The mixture was stirred for 1 h, phases were separated, the aqueous layer was extracted with dichloromethane (3×330 mL) and the combined organic extracts were concentrated in vacuo to a volume of ca. 1.1 L. Ethyl acetate (1.1 L) was added, the mixture was concentrated in vacuo to a volume of ca. 1 L and heptane (1 L) was added within 30 min. The resulting suspension was stirred for 2 h at 2° C., filtered, the precipitate was washed with cold ethyl acetate/heptane 1:1 (v/v, 340 mL) and heptane (340 mL) and dried in vacuo to afford the title compound as light yellow crystals (129.4 g, 90%). MS (ESI & APCI): m/z=278.1 [M+H]$^+$. $^1$H NMR (CDCl$_3$, 600 MHz): δ 0.60-0.65 (m, 2H), 0.89-0.92 (m, 1H), 0.95-0.98 (m, 1H), 1.20-1.26 (m, 2H), 1.33 (s, 3H), 1.50-1.57 (m, 2H), 2.13 (ddd, J=5.0 Hz, 9.0 Hz, 14.1 Hz, 1H), 2.39 (br d, J=14.3 Hz, 1H), 3.76 (dd, J=4.3 Hz, 11.6 Hz, 1H), 3.85 (d, J=11.6 Hz, 1H), 4.48-4.53 (m, 1H), 4.57 (d, J=9.0 Hz, 1H), 4.70 (br s, 1H), 7.92 (br s, 1H).

A4. Preparation of (2S,4S)-4-hydroxy-1-(1-methyl-cyclopropanecarbonyl)-pyrrolidine-2-carboxylic acid (1-cyano-cyclopropyl)-amide a) 1-Methyl-cyclopropanecarbonyl chloride

To 1-methyl-cyclopropanecarboxylic acid (100.1 g, 1000 mmol) and DMF (0.37 g, 5.0 mmol) was carefully added under stirring at ~40° C. thionylchloride (125.0 g, 1050 mmol) over 1 h. After additional stirring at 40° C. for 1 h, the crude product (122.3 g) was distilled through a Vigreux column affording the title product (114.8 g, 96.8%) as a bright yellow liquid, bp. 129-130° C./~1000 mbar. $^1$H NMR (CDCl$_3$, 400 MHz) δ 0.98 (m, 2H), 1.40 (s, 3H), 1.59 (m, 2H).

b) (2S,4R)-4-Methanesulfonyloxy-1-(1-methyl-cyclopropanecarbonyl)-pyrrolidine-2-carboxylic acid methyl ester

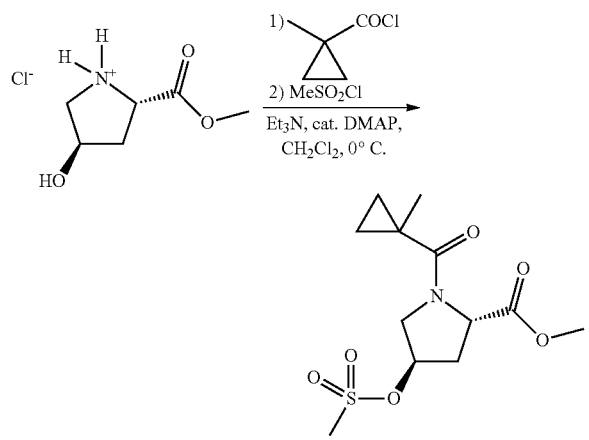

To a suspension of hydroxyproline methyl ester hydrochloride (36.3 g, 200 mol), triethylamine (65.8 g, 650 mmol) and dimethylaminopyridine (1.25 g, 10 mmol) in dichloromethane (800 mL) was added at 0° C. the 1-methyl-cyclopropanecarbonyl chloride (24.9 g, 210 mmol) over 0.5 h. After additional stirring for 2 h, methanesulfonyl chloride (28.64 g, 250 mmol; note 7) was added over 0.5 h and stirring at 0° C. was continued for 1 h. The cold reaction mixture was transferred into a separatory funnel and washed with 1 M HCl (400 mL) and 10% brine (400 mL). The aqueous layers were extracted with dichloromethane (400 mL) and the combined organic layers were dried over Na$_2$SO$_4$. Filtration and evaporation of the solvent (35-45° C./≥10 mbar) afforded crude, crystalline product (63.8 g) which was dissolved in isobutyl acetate (250 mL) at ~70° C. After seeding at ~50° C., crystallization was completed by cooling to room temperature and stirring at –20° C. overnight. Filtration and washing with cold isobutyl acetate gave after drying (50° C./10 mbar/3 h) the title product (57.5 g, 94.2%) as a white, crystalline powder, mp. 102-103° C. $[\alpha]_D^{20}$=–10.3 (c 1.0; CHCl$_3$). $^1$H NMR (CDCl$_3$, 400 MHz) δ 0.50-0.70 (m, 2H), 0.90 (m, 1H), 1.10 (m, 1H), 1.34 (s, 3H), 2.23 (m, 1H), 2.59 (m, 1H), 3.06 (s, 3H), 3.74 (s, 3H), 3.95 (d, 1H), 4.25 (d, 1H), 4.63 (br t, 1H), 5.35 (s, 1H).

c) (2S,4S)-4-Hydroxy-1-(1-methyl-cyclopropanecarbonyl)-pyrrolidine-2-carboxylic acid (1-cyano-cyclopropyl)-amide

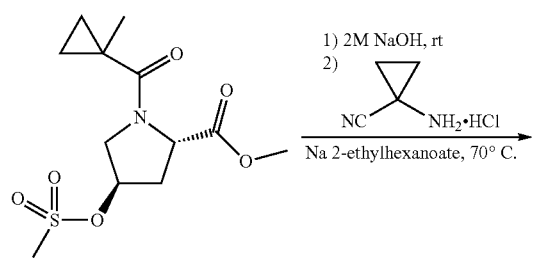

To 2 M NaOH (60.0 mL, 120 mmol) was added at 0° C. the (2S,4R)-4-methanesulfonyloxy-1-(1-methyl-cyclopropanecarbonyl)-pyrrolidine-2-carboxylic acid methyl ester (30.54 g, 100 mmol) all at once. The ice bath was removed and the white suspension was warmed to room temperature over 1 h. After the addition of 2 M HCl (10.0 mL, 20 mmol) 1-aminocyclopropanecarbonitrile hydrochloride (11.86 g, 100 mmol) and sodium 2-ethylhexanoate (18.28 g, 110 mmol) were added all at once and the biphasic reaction mixture was stirred at 70° C. for 21 h. After cooling to –35° C., dichloromethane (50 mL) and NaCl (8.0 g) were added and stirring was continued until the NaCl was dissolved. The reaction mixture was acidified with 25% HCl (8 mL), transferred into a separatory funnel, and extracted with dichloromethane (4×150 mL). All four organic layers were washed sequentially with 5% NaHCO$_3$ (20 mL). The combined organic layers were dried (Na$_2$SO$_4$), filtered, and evaporated to dryness (40° C./≥5 mbar) affording a beige, crystalline residue (38.5 g) which was redissolved in dichloromethane (200 mL). Solvent exchange with ethyl acetate was accomplished at the rotary evaporator by portion-wise addition of ethyl acetate (350 mL) at 60-80° C./950 mbar and at the same time distilling off dichloromethane. The crystal suspension was cooled to room temperature and stirred at –20° C. over night. Filtration and washing with cold ethyl acetate afforded after drying (50° C./10 mbar/4 h) the title product (20.8 g, 75.0%) as an off white, crystalline powder, mp. 159.5-160.5° C. $[\alpha]_D^2$=–111.0 (c 1.0; CHCl$_3$). $^1$H NMR (CDCl$_3$, 400 MHz) δ 0.58-0.67 (m, 2H), 0.86-1.02 (m, 2H), 1.18-1.28 (m, 2H), 1.33 (s, 3H), 1.48-1.59 (m, 2H), 2.09-2.18 (m, 1H), 2.36 (d, J=14 Hz, 1H), 3.76 and 3.86 (AB, J$_{AB}$=11.7 Hz, J$_{AX}$=4.3 Hz, J$_{BX}$=0 Hz, each 1H), 4.50 (quint, J=4.6 Hz, 1H), 4.55 (d, J=8.9 Hz, 1H), 4.75 (d, J=9.1 Hz, 1H), 7.98 (s, 1H).

B. Thio Compound Formation

B1. Preparation of 2-chloro-4-((S)-2,2,2-trifluoro-1-methyl-ethoxy)-benzenethiol a) 2-Chloro-4-fluoro-1-tritylsulfanyl-benzene

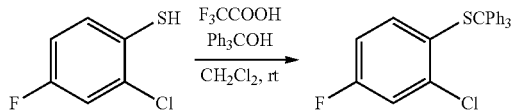

2-Chloro-4-fluoro-benzenethiol (250 g, 1.54 mol) was dissolved in dichloromethane (1.25 L) and trifluoroacetic acid (120 mL, 1.57 mol) followed by triphenylmethanol (400 g, 1.54 mol) were added at room temperature (ice bath cooling necessary during addition of triphenylmethanol). The mixture was stirred for 1.5 h at room temperature, concentrated and dried in vacuo to yield the title compound as a yellow solid (622 g, 99% purity by HPLC, 99%), that was used without further purification in the next step. $^1$H NMR (CDCl$_3$, 400 MHz): δ 6.55 (ddd, J=2.9 Hz, 8.0 Hz, 8.9 Hz, 1H), 6.91 (dd, J=6.2 Hz, 8.9 Hz, 1H), 6.97 (dd, J=2.9 Hz, 8.6 Hz, 1H), 7.20-7.27 (m, 9H), 7.34-7.39 (m, 6H).

b) 2-Chloro-4-((S)-2,2,2-trifluoro-1-methyl-ethoxy)-1-tritylsulfanyl-benzene

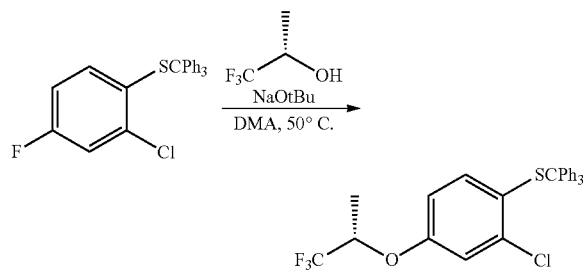

(S)-1,1,1-Trifluoro-propan-2-ol (100 g, 877 mmol) was dissolved in dimethylacetamide (600 mL) and the solution was cooled to 2° C. (ice bath). A solution of sodium tert-butoxide (77.5 g, 790 mmol) in dimethylacetamide (100 mL) was added at 2° C. and the mixture was stirred for 15 min. This solution was treated with a solution of 2-chloro-4-fluoro-1-tritylsulfanyl-benzene (200 g, 494 mmol) in dimethylacetamide (100 mL) at room temperature and subsequently stirred for 3 h at 50° C. It was then poured into a mixture of brine (200 mL), ice (1.2 kg) and water (2.0 L), and extracted with tert-butyl-methylether (2×1000 mL). The combined organic extracts were washed with brine/water 1:1 (v/v, 300 mL) and concentrated in vacuo to give the crude product as a yellow viscous oil. The oil was dissolved in ethanol (1.6 L), before water (240 mL) was slowly added at room temperature. The resulting suspension was stirred for 14 h, cooled to 2° C. (ice bath) and stirred for another 2 h, before it was filtered. The solid was washed with ethanol/water 4:1 (v/v, 500 mL) and dried in vacuo to afford the title compound as a white crystalline solid (238 g, 97%). $^1$H NMR (CDCl$_3$, 400 MHz): δ 1.43 (d, J=6.5 Hz, 3H), 4.50 (qq, J=6.2 Hz, 6.2 Hz, 1H), 6.44 (dd, J=2.8 Hz, 8.7 Hz, 1H), 6.84 (d, J=2.7 Hz, 1H), 6.90 (d, J=8.6 Hz, 1H), 7.18-7.27 (m, 9H), 7.33-7.39 (m, 6H).

c) 2-Chloro-4-((S)-2,2,2-trifluoro-1-methyl-ethoxy)-benzenethiol

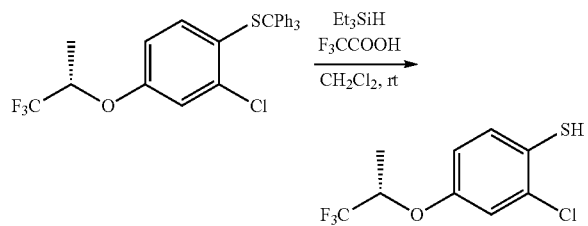

2-Chloro-4-((S)-2,2,2-trifluoro-1-methyl-ethoxy)-1-tritylsulfanyl-benzene (220 g, 441 mmol) was dissolved in dichloromethane (800 mL) and trifluoroacetic acid (165 mL, 2.15 mol) was added at room temperature, followed by triethylsilane (110 mL, 674 mmol, ice bath cooling necessary). After stirring for 30 min at room temperature, the mixture was concentrated in vacuo. A potassium hydroxide solution (2M in water, 1.1 L) was added to the residue, and the suspension was stirred for 15 min. After filtration, the remaining solid was washed with water. The combined filtrate was acidified to pH<2 by addition of hydrochloric acid (25% in water, 330 mL) and extracted with tert-butyl-methylether (3×500 mL). The combined organic extracts were washed with an aqueous potassium hydrogencarbonate solution (1M, 330 mL), dried over sodium sulfate, and concentrated in vacuo. The turbid oil was treated with heptane (80 mL) and filtered. The remaining solid was further washed with heptane (20 mL). The combined filtrate was concentrated and dried in vacuo to yield the title compound as a colorless liquid (105 g, 93%). $^1$H NMR (CDCl$_3$, 400 MHz): δ 1.49 (dd, J=6.5 Hz, 0.5 Hz, 3H), 3.75 (s, 1H), 4.55 (qq, J=6.2 Hz, 6.2 Hz, 1H), 6.79 (dd, J=3.0 Hz, 8.9 Hz, 1H), 7.03 (d, J=2.7 Hz, 1H), 7.29 (d, J=8.6 Hz, 1H).

B2. Preparation of 4-(2,2,2-trifluoro-ethoxy)-2-trifluoromethyl-benzenethiol a) 4-Fluoro-2-trifluoromethyl-1-tritylsulfanyl-benzene

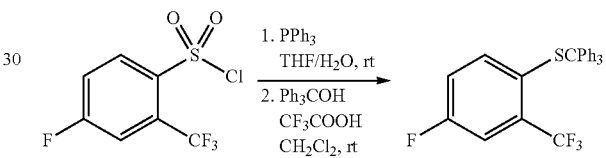

Triphenylphosphine (126.2 g, 481 mmol) was dissolved in tetrahydrofuran (155 mL) and a solution of 4-fluoro-2-trifluoromethyl-benzenesulfonyl chloride (40.0 g, 152 mmol) in tetrahydrofuran (80 mL) was added within 30 min at 22° C. internal temperature. The yellow suspension was stirred for 15 min at room temperature, then water (48 mL) was added and the resulting clear solution stirred for 20 min. Concentrated sodium hydroxide solution (32% m/m in water, 34 mL, 367 mmol) and water (260 mL) were added, the tetrahydrofuran was distilled off completely in vacuo and the resulting aqueous suspension was filtered. The filtered solids (triphenylphosphine and triphenylphosphine oxide) were washed thoroughly with water (360 mL), the combined filtrates were acidified by addition of aqueous hydrochloric acid (25% m/m in water, 40.0 mL, 307 mmol), extracted with dichloromethane (1×200 mL, 1×60 mL) and the combined organic extracts (ca. 260 mL) were used in the following step without further treatment.

Triphenylmethanol (39.7 g, 149.4 mmol) was dissolved in the solution of crude 4-fluoro-2-trifluoromethyl-benzenethiol in dichloromethane (ca. 260 mL) of the preceding step and a solution of trifluoroacetic acid (21.2 g, 186 mmol) in dichloromethane (20 mL) was added at room temperature. After stirring for 15 h, the mixture was basified by subsequent addition of water (20 mL), concentrated aqueous sodium hydroxide solution (32% m/m, 26.9 g, 215 mmol) and water again (240 mL). Phases were separated, the aqueous layer was extracted with dichloromethane (100 mL) and the combined organic extracts concentrated in vacuo at 50° C. to a volume of ca. 330 mL. Ethanol (400 mL) was continuously added to the distillation, while the overall volume was kept constant (solvent exchange). The solution (ca. 300 mL) was allowed to cool to room temperature, crystallization started at 42° C. The suspension was stirred for 18 h at room temperature and for 1 h at 0° C. After filtration, the precipitate was washed with cold ethanol (100 mL) and dried in vacuo at 40° C. to give rise to the title compound as a white crystalline solid (52.5 g, 79%). MS (EI): m/z=243 [CPh₃]⁺. ¹H NMR (CDCl₃, 600 MHz): δ 6.73 (ddd, J=2.8 Hz, 8.3 Hz, 8.3 Hz, 1H), 7.04 (dd, J=5.4 Hz, 8.8 Hz, 1H), 7.18-7.25 (m, 10H), 7.35-7.37 (m, 6H). Anal. Calcd for C26H18F4S: C, 71.22; H, 4.14; S, 7.31; F, 17.33. Found: C, 71.16; H, 4.26; S, 7.15; F, 17.09.

b) 4-(2,2,2-Trifluoro-ethoxy)-2-trifluoromethyl-1-tritylsulfanyl-benzene

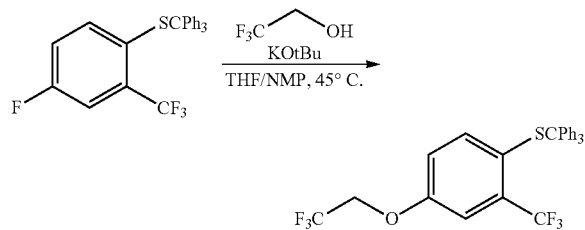

Potassium tert-butoxide (98% m/m, 39.17 g, 342.1 mmol) was suspended in tetrahydrofuran (190 mL) and a solution of trifluoroethanol (35.65 g, 356.4 mmol) in tetrahydrofuran (28 mL) was added at room temperature (exothermic). The mixture was stirred for 15 min, and a solution of 4-fluoro-2-trifluoromethyl-1-tritylsulfanyl-benzene (125 g, 285 mmol) in 1-methyl-2-pyrrolidon (240 mL) and tetrahydrofuran (290 mL) was added. The resulting brown solution was stirred for 30 min at room temperature, followed by 2 h at 45° C. internal temperature. After that, water (720 mL), brine (125 mL), and tert-butyl-methylether (720 mL) were added and phases were separated. The organic layer was washed with a solution of sodium chloride (59.3 g, 1015 mmol) in water (380 mL) and concentrated in vacuo at 40° C. to a volume of ca. 400 mL. The solution was diluted with ethanol (300 mL), and additional ethanol (480 mL) was continuously added to the distillation, while the overall volume was kept constant at ca. 700 mL (solvent exchange). The resulting suspension was stirred for 14 h at room temperature and 1 h at 0° C. before water (140 mL) was added and the suspension was stirred for further 1.5 h at 0° C. After filtration, the precipitate was washed with cold ethanol/water 5:1 (v/v, 288 mL) and dried in vacuo to yield the title compound as fine yellow crystals (140.9 g, 95%). MS (EI): m/z=243 [CPh₃]⁺. ¹H NMR (CDCl₃, 600 MHz): δ 4.26 (q, J=8.0 Hz, 2H), 6.61 (dd, J=2.9 Hz, 8.8 Hz, 1H), 7.04 (d, J=8.8 Hz, 1H), 7.07 (d, J=2.9 Hz, 1H), 7.18-7.25 (m, 9H), 7.33-7.37 (m, 6H).

c) 4-(2,2,2-Trifluoro-ethoxy)-2-trifluoromethyl-benzenethiol

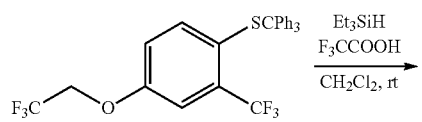

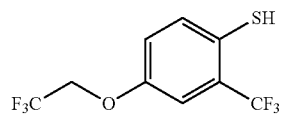

4-(2,2,2-Trifluoro-ethoxy)-2-trifluoromethyl-1-tritylsulfanyl-benzene (100 g, 193 mmol) was dissolved in dichloromethane (600 mL) and trifluoroacetic acid (44.9 g, 386 mmol) was added at room temperature, followed by a solution of triethylsilane (24.9 g, 214 mmol) in dichloromethane (75 mL) at 18° C. (ice bath cooling). The yellow mixture was stirred for 3 h at room temperature. Water (600 mL) was then added and dichloromethane was distilled off in vacuo under vigorous stirring. Tert-butyl-methylether (600 mL) was added and the resulting biphasic mixture was basified by addition of a concentrated aqueous sodium hydroxide solution (32% m/m, 54 mL, 583 mmol) to pH 12. Phases were separated, the aqueous layer was extracted with tert-butyl-methylether (400 mL), acidified by addition of hydrochloric acid (25% m/m in water, 35 mL, 268 mmol) to pH 3, and extracted with tert-butyl-methylether (600 mL). The organic extract was washed with a solution of sodium hydrogencarbonate (16.1 g, 193 mmol) in water (500 mL), and water (500 mL) and concentrated in vacuo to afford the title compound as a light yellow liquid (49.7 g, 90%). MS (ESI & APCI, neg): m/z=275.0 [M−H]⁺. ¹H NMR (CDCl₃, 600 MHz): δ3.66 (q, J=2.5 Hz, 1H), 4.36 (q, J=8.0 Hz, 2H), 6.99 (dd, J=2.9 Hz, 8.6 Hz, 1H), 7.23 (d, J=2.8 Hz, 1H), 7.39 (d, J=8.6 Hz, 1H).

B3. Preparation of 4-(2,2,2-trifluoro-ethoxy)-2-trifluoromethyl-benzenethiol a1) 1-Bromo-4-(2,2,2-trifluoro-ethoxy)-2-trifluoromethyl-benzene

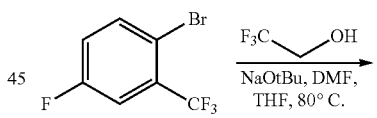

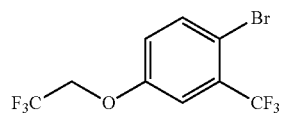

To a 2.4 M solution of sodium-tert-butoxide in THF (156.3 mL, 375 mmol, Chemetall) was added DMF (38.5 mL, 500 mmol) and then 2,2,2-trifluoroethanol (41.27 g, 413 mmol). After the addition of 2-bromo-5-fluorobenzotrifluoride (60.8 g, 250 mmol) the reaction mixture was heated to reflux and stirred at ~80° C. for 7 h. After cooling to 25° C., TBME (800 mL) was added and the reaction mixture was washed with 1M HCl (400 mL), 5% NaHCO₃ (400 mL) and 10% brine (400 mL). The organic layer was dried (Na₂SO₄), filtered and evaporated to dryness (60° C./≥5 mbar), affording the crude title product (80.0 g, 99.1%) as a yellow oil which was used without purification in the next step ¹H NMR (CDCl₃, 400

MHz) δ 4.38 (q, J=7.9 Hz, 2H), 6.98 (dd, J₁=8.6 Hz, J₂=2.7 Hz, 1H), 7.28 (d, J=2.7 Hz, 1H), 7.65 (d, J=8.9 Hz, 1H).

b1) 4-(2,2,2-Trifluoro-ethoxy)-2-trifluoromethyl-benzenethiol

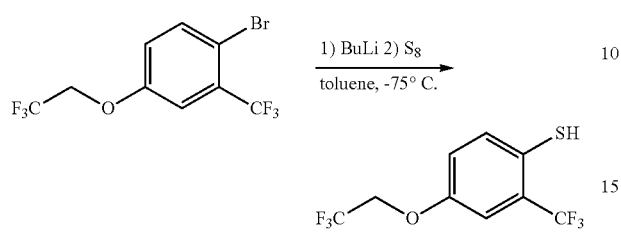

To a solution of 1-bromo-4-(2,2,2-trifluoro-ethoxy)-2-tri-fluoromethyl-benzene (80.8 g 250 mmol) in toluene (1000 mL) was added diethyl ether (52 mL, 500 mmol). After cooling to −75° C., 2.5 M butyllithium in toluene (105 mL, 263 mmol) was added at −75° C. over 30 min and stirring at −75° C. was continued for 30 min. Sulfur powder (8.8 g, 275 mmol) was then added at −75° C. all at once and stirring was continued for 7 h. The cold yellow suspension was poured to a stirred mixture of toluene (1000 mL) and 0.5M NaOH (1000 mL). After vigorous stirring for 5 min the two layers were separated and the aqueous layer was extracted with toluene (500 mL). The aqueous layer was cooled to ~10° C., acidified with 6M HCl (~150 mL) and extracted with dichloromethane (1000 mL). The dichloromethane layer was washed with 10% brine (1000 mL), dried with Na₂SO₄, filtered and evaporated to dryness (60° C./≥5 mbar) affording crude yellow oily product (58.2 g). Purification by distillation gave the title product (55.1 g, 79.8%) as bright yellow oil, bp. 84-86° C./2.3 mbar. ¹H NMR (CDCl₃, 400 MHz) δ 3.66 (q, J=2.4 Hz, 1H), 4.36 (q, J=8.1 Hz, 2H), 6.98 (dd, J₁=8.6 Hz, J₂=2.7 Hz, 1H), 7.23 (d, J=2.7 Hz, 1H), 7.39 (d, J=8.6 Hz, 1H).

b2) 4-(2,2,2-Trifluoro-ethoxy)-2-trifluoromethyl-benzenethiol

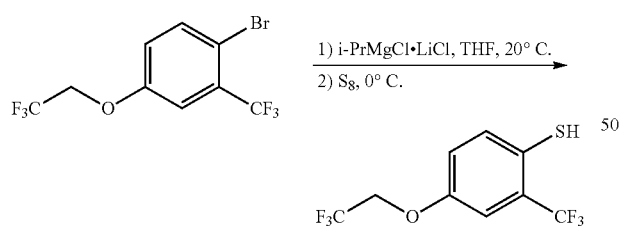

To a solution of 1-bromo-4-(2,2,2-trifluoro-ethoxy)-2-tri-fluoromethyl-benzene (16.2 g, 50 mmol) in THF (200 mL) was added at 20° C. under stirring 1.3 M isopropylmagnesium chloride/lithium chloride (1:1) in THF (46.2 mL≅45.2 g, 60 mmol Turbo-Grignard, Chemetall) over 30 min. After stirring at 20° C. for 2 h the clear, yellow solution was cooled to 0° C. and sulfur powder (1.84 g, 57.5 mmol) was added all at once. Stirring at 0° C. was continued for 2 h and the reaction mixture was hydrolyzed under vigorous stirring with 0.5 M HCl (200 mL) and extracted twice with TBME (200 mL & 100 mL). The two organic layers were washed with 0.5 M NaOH (200 mL), the NaOH layer was acidified under ice cooling with 6 M HCl (20 mL) and extracted with TBME (200 mL). The TBME layer was washed with 10% brine (100 mL), dried (Na2SO4), filtered and evaporated (≤60° C./≥5 mbar) affording the crude title product (11.4 g) as a yellow oil which was purified by Kugelrohr distillation (11.1 g, 80.4%), bp.≈90° C./2 mbar. ¹H NMR (CDCl₃, 400 MHz.) δ 3.66 (q, J=2.4 Hz, 1H), 4.36 (q, J=8.1 Hz, 2H), 6.98 (dd, J₁=8.6 Hz, J₂=2.7 Hz, 1H), 7.23 (d, J=2.7 Hz, 1H), 7.39 (d, J=8.6 Hz, 1H).

B4. Preparation of 2-chloro-4-((S)-2,2,2-trifluoro-1-methyl-ethoxy)-benzenethiol a) 1-bromo-2-chloro-4-((S)-2,2,2-trifluoro-1-methyl-ethoxy)-benzene

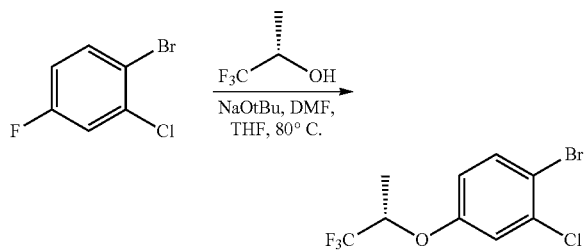

To 2.4 M sodium-tert-butoxide in THF (156.3 mL, 375 mmol) was added under stirring (S)-1,1,1-trifluoro-propan-2-ol (47.1 g, 413 mmol), DMF (77.0 mL, 1000 mmol) and 1-bromo-2-chloro-4-fluoro-benzene (52.4 g, 250 mmol). The reaction mixture was heated to reflux and stirred at ~80° for 19 h. After cooling to room temperature TBME (1000 mL) was added and the reaction mixture was washed with 1M HCl (500 mL), 5% NaHCO3 (500 mL) and 10% brine (400 mL). The aqueous layers were extracted with TBME (400 mL) and the organic layers was dried (Na₂SO₄), filtered and evaporated to dryness (≤60° C./≥5 mbar) affording 75.8 g crude title product. Distillation through a Vigreux column was gave as colorless oil (71.5 g, 94.2%), bp. ~70° C./0.1 mbar. ¹H NMR (CDCl₃, 400 MHz) δ 1.50 (dd, J₁=6.4 Hz, J₂=0.5 Hz, 3H), 4.59 (hept, J=6.2 Hz, 1H), 6.76 (dd, J₁=8.9 Hz, J₂=3.0 Hz, 1H), 7.09 (d, J=2.7 Hz, 1H), 7.52 (d, J=8.9 Hz, 1H).

b) 2-Chloro-4-((S)-2,2,2-trifluoro-1-methyl-ethoxy)-benzenethiol

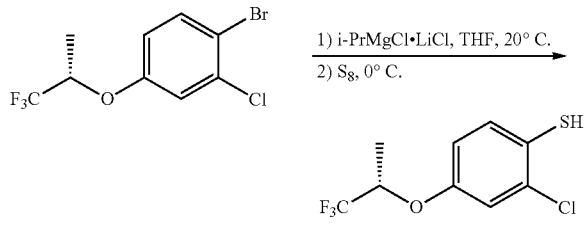

To a solution of 1-bromo-2-chloro-4-((S)-2,2,2-trifluoro-1-methyl-ethoxy)-benzene (15.2 g, 50 mmol) in THF (200 mL) was added under stirring at 20° C. 1.3 M isopropylmagnesium chloride/lithium chloride (1:1) in THF (50.0 mL≅49.0 g, 65 mmol Turbo-Grignard, Chemetall) over 30 min. After additional stirring at 20° C. for 2 h the yellow solution was cooled to −5° C. and Sulfur (1.92 g, 60 mmol) was added all at once. After stirring at 0° C. for 2 h the ice bath was removed and the reaction mixture was hydrolyzed with 1 M HCl (125 mL). The reaction mixture was extracted twice with TBME (200 mL & 100 mL) and the organic layers were washed with 1 M NaOH (125 mL). The NaOH layer was separated, cooled to −10° C. and acidified with 6 M HCl (25 mL). After extraction with TBME (200 mL) and washing with 10% brine (100 mL) the organic layer was dried (Na$_2$SO$_4$), filtered and evaporated (≤50° C./≥5 mbar) affording (10.1 g, 78.7%) crude title product as a yellow oil. $^1$H NMR (CDCl$_3$, 400 MHz) δ 1.49 (dd, J$_1$=6.5 Hz, J$_2$=0.5 Hz, 3H), 3.75 (s, 1H), 4.55 (hept, J=6.2 Hz, 1H), 6.79 (d×d, J$_1$=8.9 Hz, J$_2$=3.0 Hz, 1H), 7.03 (d, J=2.7 Hz, 1H), 7.29 (d, J=8.6 Hz, 1H).

B5. Preparation of 3-[4-(2-methyl-pyridin-4-yl)-2-trifluoromethyl-phenylsulfanyl]-propionamide a) 4-Bromo-2-trifluoromethyl-benzenethiol

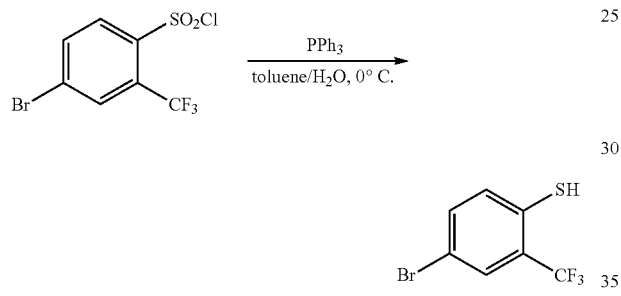

4-Bromo-2-trifluoromethyl-benzenesulfonyl chloride (375 g, 1.16 mol) was dissolved in toluene (1.5 L) and a solution of triphenylphosphine (994 g, 3.79 mol) in toluene (1.5 L) was added at 5-10° C. within 45 min. The yellow suspension was stirred at 0-5° C. for min, then water (360 mL) was added at 5-12° C. (strongly exothermic) and the resulting colorless suspension was stirred for 20 min at room temperature. After filtration, the precipitate was washed with toluene (1 L). The combined organics were extracted with a potassium hydroxide solution (1M in water, 2.8 L). During extraction, 3 layers were formed. The upper layer was discarded, the other two were washed with toluene (1 L). The aqueous phase was acidified to pH 3-4 by addition of citric acid (280 g, 1.46 mol). After addition of n-heptane (1 L), the precipitate was filtered off and washed with n-heptane (500 mL). The layers of the combined filtrate were separated and the aqueous phase was extracted with n-heptane (1.5 L). The combined organic extracts were dried over sodium sulfate. Silica gel (250 g) was then added, the slurry was stirred for 10 min at room temperature, filtered and the filtered silica gel washed with n-heptane (1 L). The combined filtrate was concentrated and dried in vacuo at 45° C. to afford 291.2 g (98%) of the title compound as a colorless liquid that was used without further purification in the next step. MS (EI): m/z=256.9, 254.9 [M+H]+. $^1$H NMR (CDCl$_3$, 400 MHz): δ 3.76 (q, J=2.8 Hz, 1H), 7.26 (d, J=8.3 Hz, 1H), 7.48 (dd, J=2.0 Hz, 8.5 Hz, 1H), 7.75 (d, J=1.9 Hz, 1H).

b) 3-(4-Bromo-2-trifluoromethyl-phenylsulfanyl)-propionamide

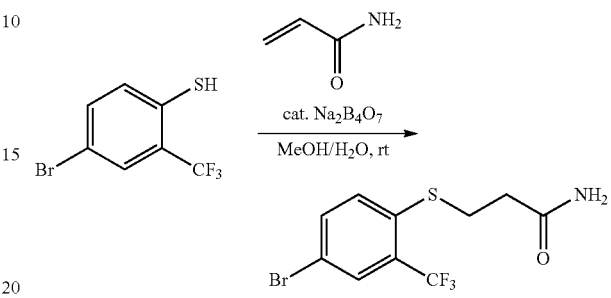

4-Bromo-2-trifluoromethyl-benzenethiol (259.2 g, 1.01 mol) was dissolved in methanol (1.3 L) and water (2.6 L), then acrylamide (130 g, 1.82 mol), followed by sodium tetraborate (25.9 g, 129 mmol) were added at room temperature. The suspension was stirred for 40 h. After filtration, the solid was washed with water (2.6 L) and n-heptane (2.6 L) and dried in vacuo to yield the title compound as a white powder (325.6 g, 98%). MS (EI): m/z=330.0, 328.0 [M+H]$^+$. $^1$H NMR (d6-DMSO, 400 MHz): δ 2.40 (t, J=7.2 Hz, 2H), 3.24 (t, J=7.2 Hz, 2H), 6.92 (bs, 1H), 7.37 (bs, 1H), 7.60 (d, J=8.3 Hz, 1H), 7.82-7.88 (m, 2H).

c1) 3-[4-(2-Methyl-pyridin-4-yl)-2-trifluoromethyl-phenylsulfanyl]-propionamide

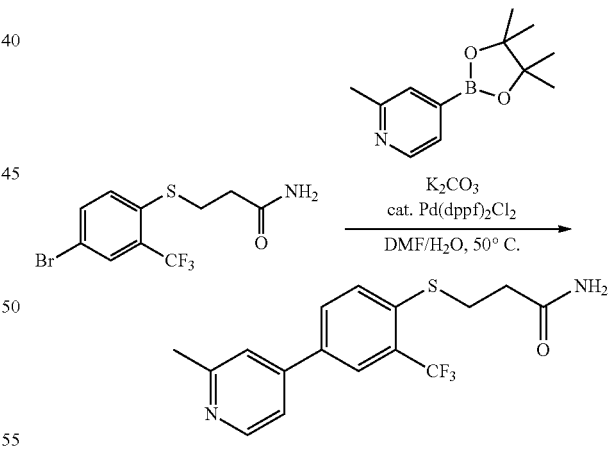

3-(4-Bromo-2-trifluoromethyl-phenylsulfanyl)-propionamide (300 g, 914 mmol) was dissolved in N,N-dimethylformamide (3.0 L) and potassium carbonate (300 g, 2.17 mol). Then, 2-methylpyridine-4-boronic acid pinacol ester (285 g, 1.3 mol) and water (240 mL) were added. The solution was degassed and [1,1'-bis(diphenylphosphino)ferrocene]dichloropalladium(II) (30 g, 41 mmol) was added. The mixture was stirred for 20 h at 50° C. After cooling to room temperature, it was poured onto ice cold water (5° C., 5 L) and extracted with ethyl acetate (1×3.5 L, 2×1.5 L). The combined organic extracts were washed with brine/water (1:1 v/v, 750 mL) and brine (750 mL), before methanol (600 mL) was added and the mixture was dried over sodium sulfate. Silica gel (400 g) was added, the slurry was filtered and washed with ethyl acetate/methanol (9:1 v/v, 1.5 L). The combined filtrates were concentrated in vacuo. The residue was suspended in toluene (600 mL) and n-heptane (300 mL) and stirred for 5 min at 60° C. and for 1 h at room temperature. The precipitate was filtered off, washed with toluene/n-heptane (4:1 v/v, 300 mL) and n-heptane (300 mL), and dried in vacuo to afford 230.3 g of brown crystalline material. The crystals were further purified by trituration in isopropanol/heptane (1:1 v/v, 600 mL) for 30 min at room temperature and 30 min at 0-4° C. (ice bath). The precipitate was filtered off, washed with n-heptane/isopropanol (4:1 v/v, 300 mL), and dried in vacuo at 65° C. to yield the title compound as a light brown crystalline solid (215.7 g, 69%). MS (EI): m/z=341.1 [M+H]. $^1$H NMR (d6-DMSO, 400 MHz): δ 2.48 (t, J=7.2 Hz, 2H), 2.54 (s, 3H), 3.32 (t, J=7.2 Hz, 2H), 6.95 (bs, 1H), 7.41 (bs, 1H), 7.58 (dd, J=1.6 Hz, 5.4 Hz, 1H), 7.68 (s, 1H), 7.77 (d, J=9.1 Hz, 1H), 8.02-8.08 (m, 2H), 8.52 (d, J=5.1 Hz, 1H).

c2) 3-[4-(2-Methyl-pyridin-4-yl)-2-trifluoromethyl-phenylsulfanyl]-propionamide (One Pot from Bromopicoline)

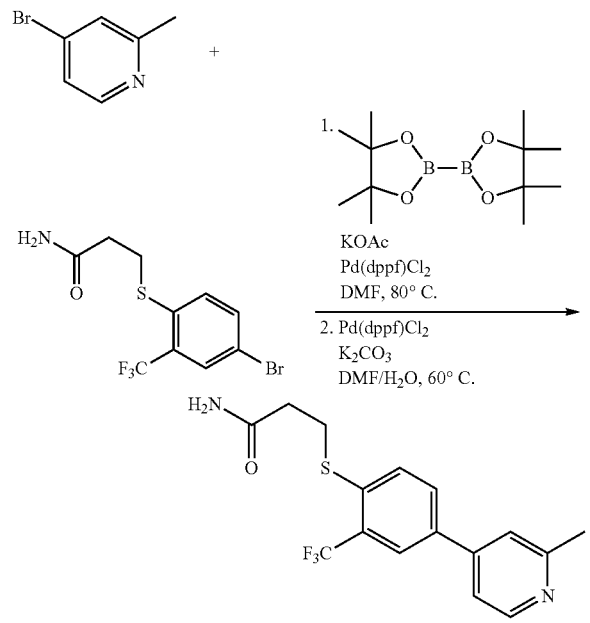

4-Bromo-2-methylpyridine (6.0 g, 34.9 mmol) was dissolved in dimethylformamide (60 mL) before potassium acetate (10.0 g, 102 mmol) and 4,4,4',4',5,5,5',5'-octamethyl-2,2'-bi(1,3,2-dioxaborolane) (10 g, 39.4 mmol) were added at room temperature. The solution was degassed and [1,1'-bis(diphenylphosphino)ferrocene]dichloropalladium(II) (400 mg, 547 mol) was added. The brown reaction mixture was stirred for 22 h at 80° C. After cooling to room temperature, 3-(4-bromo-2-trifluoromethyl-phenylsulfanyl)-propionamide (8.0 g, 24.4 mmol), potassium carbonate (8.0 g, 57.9 mmol), dimethylformamide (20 mL), and water (16 mL) were added. The mixture was degassed, stirred for 30 min at room temperature and further [1,1'-bis(diphenylphosphino)ferrocene]dichloropalladium(II) (400 mg, 547·mol) was added. The resulting brown reaction mixture was stirred for 20 h at 60° C. After cooling to room temperature, it was poured onto water (150 mL) and extracted with ethyl acetate (1×80 mL, 2×40 mL). The combined organic extracts were washed with brine/water (1:1 v/v, mL) and brine (20 mL), methanol (16 mL) was added and the mixture was dried over sodium sulfate. Silica gel (16 g) was added, the slurry was filtered and washed with ethyl acetate/methanol (9:1 v/v, 40 mL). The combined filtrates were concentrated in vacuo. The residue was treated with toluene/n-heptane (1:1 v/v, 24 mL) and the resulting suspension was stirred for 30 min at room temperature. After filtration, the precipitate was washed with toluene/n-heptane (4:1 v/v, 10 mL) and n-heptane (10 mL) and dried in vacuo to afford the title compound as brown crystals (5.7 g, 71%). MS (EI): m/z=341.1 [M+H]$^+$. $^1$H NMR (d6-DMSO, 400 MHz): δ 2.48 (t, J=7.2 Hz, 2H), 2.54 (s, 3H), 3.32 (t, J=7.2 Hz, 2H), 6.95 (bs, 1H), 7.41 (bs, 1H), 7.58 (dd, J=1.6 Hz, 5.4 Hz, 1H), 7.68 (s, 1H), 7.77 (d, J=9.1 Hz, 1H), 8.02-8.08 (m, 2H), 8.52 (d, J=5.1 Hz, 1H).

B6. Preparation of 3-[4-(1-methyl-1H-pyrazol-4-yl)-2-trifluoromethyl-phenylsulfanyl]-propionamide

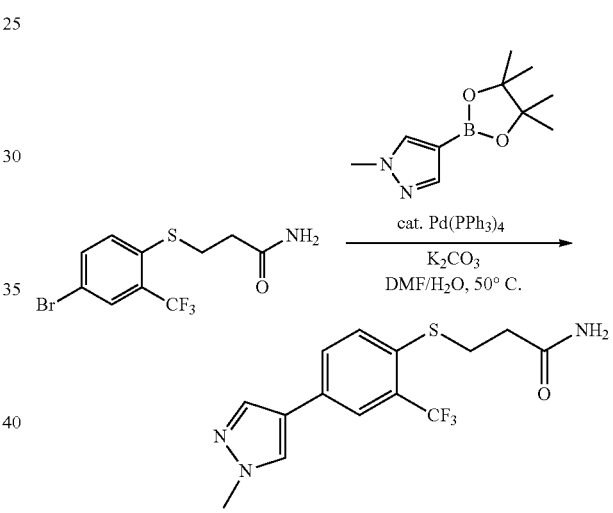

3-(4-Bromo-2-trifluoromethyl-phenylsulfanyl)-propionamide (160 g, 488 mmol) was dissolved under Ar in N,N-dimethylformamide (1.5 L) before 1-methyl-4-(4,4,5,5-tetramethyl-[1,3,2]dioxaborolan-2-yl)-1H-pyrazole (143 g, 687 mmol), potassium carbonate (160 g, 1.16 mol), and water (130 mL) were added. The solution was degassed and tetrakis-(triphenylphosphine)palladium(0) (24.0 g, 20.8 mmol) was added. The mixture was stirred for 16 h at 50° C. After cooling to room temperature, the mixture was poured onto water (5 L) and extracted with ethyl acetate (1×3 L, 2×1 L). The combined organic extracts were washed with brine (1 L), the volume was reduced in vacuo to ca. 2 L and dried over sodium sulfate. The resulting filtrate was further reduced in vacuo until precipitation occurred and a homogeneous slurry was formed. Tert-butyl methyl ether (1 L) was then added in portions to the distillation, keeping the overall volume constant (solvent exchange). The suspension was cooled to 5° C. (ice bath) and filtered. The precipitate was washed with tert-butyl methyl ether (500 mL) and dried in vacuo to provide 141 g of the title compound as brown crystalline solid (88%). MS (ESI & APCI): m/z=330.1 [M+H]. $^1$H NMR (CDCl$_3$, 600 MHz): δ 2.54 (t, J=7.4 Hz, 2H), 3.27 (t, J=7.4 Hz, 2H), 5.39

(bs, 1H), 5.52 (bs, 1H), 7.56 (s, 1H), 7.57 (s, 1H), 7.66 (s, 1H), 7.73 (bs, 1H), 7.77 (d, J=0.7 Hz, 1H).

B7. Preparation of 4-(2-methyl-pyridin-4-yl)-2-trifluoromethyl-benzenethiol hydrochloride a) 4-(4-Fluoro-3-trifluoromethyl-phenyl)-2-methyl-pyridine

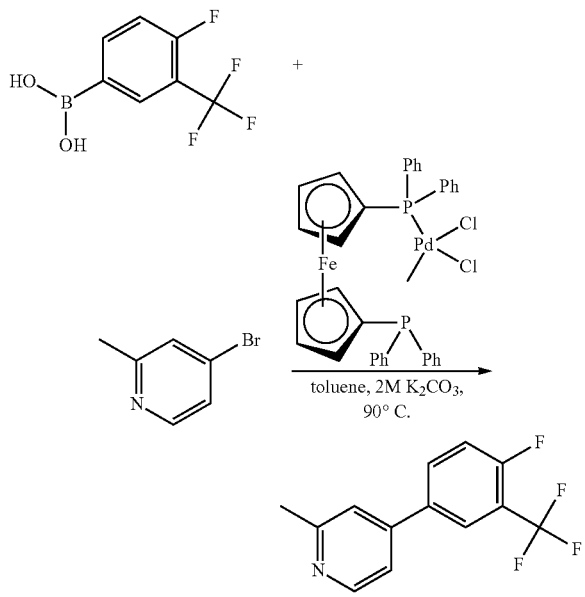

To a stirred suspension of 4-fluoro-3-(trifluoromethyl)phenylboronic acid (42.6 g, 205 mmol) in toluene (200 mL) were added 4-bromo-2-methylpyridine (34.4 g, 200 mmol) and 2 M aqueous potassium carbonate (200 mL). After the addition of 1,1'-bis(diphenylphosphino)-ferrocene-palladium(II) dichloride dichloromethane complex (81.7 mg, 0.1 mmol), the two-phase, yellowish reaction mixture was stirred under reflux at 88° C. for 23 h. The resultant brownish reaction mixture was cooled to room temperature and extracted with toluene (200 mL). After washing with 10% brine (200 mL), the toluene layer was dried with $Na_2SO_4$ (50 g) and then treated under stirring with charcoal (2 g) for 30 min. Filtration and evaporation (50° C./≥10 mbar) afforded the crude title product (50.7 g, 99.4%) as an off-white, crystalline residue which was used without purification in the next step. $^1$H NMR (CDCl$_3$, 400 MHz) δ 2.64 (s, 3H), 7.25-7.36 (m, 3H), 7.76-7.82 (m, 1H), 7.84 (dd, J$_1$=6.7 Hz, J$_2$=2.4 Hz, 1H), 8.58 (d, J=5.0 Hz, 1H). ESI-MS (m/z) [M+H]$^+$256.3 (100).

b) 4-(4-tert-Butylsulfanyl-3-trifluoromethyl-phenyl)-2-methyl-pyridine

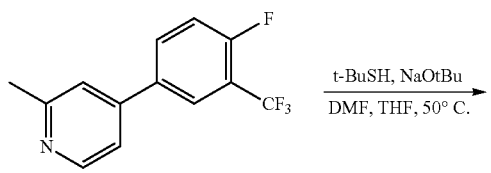

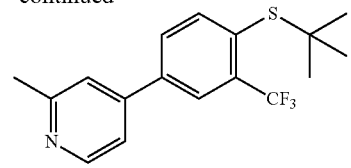

To a solution of 4-(4-Fluoro-3-trifluoromethyl-phenyl)-2-methyl-pyridine (51.0 g, ~200 mmol) in THF (100 mL) were carefully added at room temperature 2-methyl-2-propanethiol (23.5 g, 260 mmol) and DMF (29.2 g, 400 mmol). Sodium-tert-butoxide solution 25% in THF (96.1 g=106 mL, 250 mmol, Chemetall) was added over 50 min and the beige suspension was stirred at 50° C. for 17 h. The brownish suspension was transferred into a separatory funnel, filled with TBME (500 mL), and washed with water (500 mL) and with 10% brine (500 mL). The two aqueous layers were extracted with TBME (300 mL) and the combined organic layers were dried (Na$_2$SO$_4$). Filtration and evaporation (45° C./≥10 mbar) afforded crude title product (65.5 g, 100.6%) as a brown oil which was used without purification in the next step. $^1$H NMR (CDCl$_3$, 400 MHz) δ 1.39 (s, 9H), 2.65 (s, 3H), 7.33 (d, J=5.1 Hz, 1H), 7.39 (s, 1H), 7.73 (dd, J$_1$=8.1 Hz, J$_2$=1.9 Hz, 1H), 7.83 (d, J=8.1 Hz, 1H), 7.96 (d, J=1.9 Hz, 1H), 8.60 (d, J=5.4 Hz, 1H). ESI-MS (m/z) [M+H]$^{+326}$ (100).

c) 4-(2-Methyl-pyridin-4-yl)-2-trifluoromethyl-benzenethiol hydrochloride

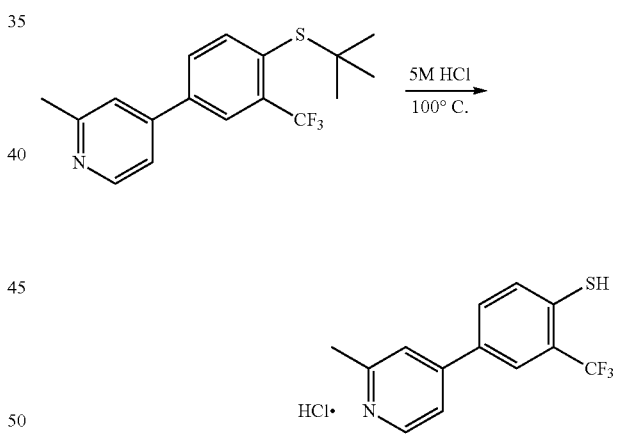

4-(4-tert-Butylsulfanyl-3-trifluoromethyl-phenyl)-2-methyl-pyridine (65.1 g, ~200 mmol) was dissolved in 5 M HCl (800 mL) and the yellowish solution was warmed up and stirred at 100° C. under reflux for 22 h. After cooling (~1 h) and stirring at room temperature for 0.5 h, the beige suspension was filtered and the filter cake was washed with deionized water (400 mL) and acetone (200 mL) and then dried (50° C./≥10 mbar/24 h) to give 57.4 g (93.9%) of the title compound as an off-white, crystalline powder, mp. >270° C. (dec.). $^1$H NMR (CDCl$_3$+2 drops TFA, 400 MHz) δ 2.96 (s, 3H), 4.06 (q, J=3.3 Hz, 1H), 7.63 (d, J=8.3 Hz, 1H), 7.74 (dd, J$_1$=8.3 Hz, J$_2$=2.1 Hz, 1H), 7.84 (d, J=1.9 Hz, 1H), 7.93 (dd, $J_1$=6.3 Hz, $J_2$=1.9 Hz, 1H), 7.97 (d, J=1.9, 1H), 8.79 (d, J=6.2 Hz, 1H), 9.96 (s, 14H, TFA), 15.18 (br s, 1H). ESI-MS (m/z) [M−HCl]⁻ 270 (100).

B8. Preparation of 4-(1-methyl-1H-pyrazol-4-yl)-2-trifluoromethyl-benzenethiol

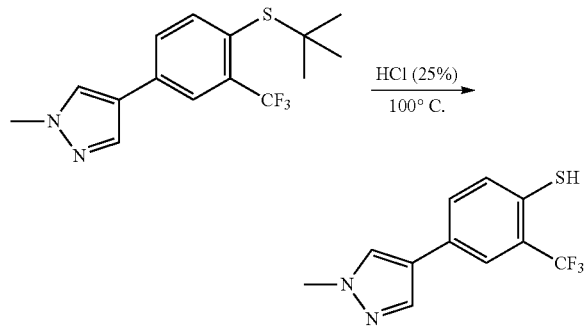

4-(4-tert-Butylsulfanyl-3-trifluoromethyl-phenyl)-1-methyl-1H-pyrazole (40.0 g, 127 mmol) was suspended in hydrochloric acid (25% w/w, 780 mL) and stirred at 100° C. under reflux. Part of the hydrochloric acid was distilled off (ca. 80 mL). After the reaction was complete as shown by HPLC, it was cooled to 85° C., water (240 mL) was added, and the mixture was cooled further to 20° C. The pH was adjusted to 4.0 by addition of a solution of sodium hydroxide (32% w/w, ca. 480 mL) in water (960 mL). The aqueous phase was extracted with 2-methyltetrahydrofuran (2×320 mL), the combined organic extracts were washed with a solution of sodium chloride (40.0 g) in water (400 mL) and concentrated in vacuo. The residue was redissolved in tetrahydrofuran (260 mL), concentrated in vacuo, dissolved again in tetrahydrofuran (110 mL) and filtered in order to remove inorganic salts. The precipitate was washed with tetrahydrofuran (30 mL) and the combined filtrate was concentrated in vacuo to obtain the title compound as light brown solid (32.4 g, 98.6%), that was used without further purification in the next step.

C. Product Formation

C1. Preparation of (2S,4R)-4-[2-chloro-4-((S)-2,2,2-trifluoro-1-methyl-ethoxy)-benzenesulfonyl]-1-(1-trifluoromethyl-cyclopropanecarbonyl)-pyrrolidine-2-carboxylic acid (1-cyano-cyclopropyl)-amide a) Benzenesulfonic acid (3S,5S)-5-(1-cyano-cyclopropylcarbamoyl)-1-(1-trifluoromethyl-cyclopropanecarbonyl)-pyrrolidin-3-yl ester

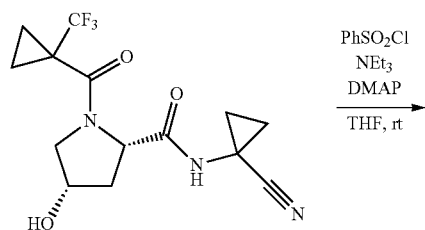

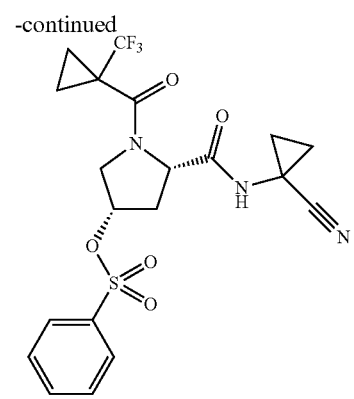

(2S,4S)-4-Hydroxy-1-(1-trifluoromethyl-cyclopropanecarbonyl)-pyrrolidine-2-carboxylic acid (1-cyano-cyclopropyl)-amide (100.0 g, 301.8 mmol) was dissolved in tetrahydrofuran (500 mL). The mixture was cooled to 2° C. (ice bath), benzenesulfonyl chloride (99%, 48 mL, 370.5 mmol), 4-(dimethylamino)pyridine (98%, 2.0 g, 16.0 mmol), and triethylamine (75.0 mL, 539 mmol) were added subsequently and the mixture was stirred for 15 min. The reaction was allowed to warm to room temperature and stirred for 20 h. After cooling to 2° C. (ice bath), water (150 mL) and methanol (350 mL) were added. Tetrahydrofuran was distilled off carefully in vacuo (ca. 500 mL) and water (500 mL) was added slowly. After addition of 300 mL water, crystallization was induced by addition of seed crystals. The resulting suspension was stirred for 30 min at 2° C. (ice bath) and filtered. The solid was washed with methanol/water 1:2 (v/v, 300 mL) and heptane (300 mL) and dried in vacuo to afford the title compound as off-white crystals (140.8 g, 99%). ¹H NMR (CDCl₃, 400 MHz): δ 1.06-1.27 (m, 4H), 1.28-1.41 (m, 2H), 1.44-1.54 (m, 2H), 2.26 (ddd, J=5.9 Hz, 9.4 Hz, 14.2 Hz, 1H), 2.59 (ddd, J=3.8 Hz, 3.8 Hz, 14.2 Hz, 1H), 3.90 and 4.03 (ABX, $J_{AB}$=12.5 Hz, $J_{Ax}$=4.0 Hz, $J_{BX}$=5.2 Hz, each 1H), 4.57 (br d, J=5.1 Hz, 1H), 5.02-5.09 (m, 1H), 7.08 (br s, 1H), 7.61 (t, J=7.8 Hz, 2H), 7.71 (t, J=7.5 Hz, 1H), 7.95 (d, J=7.2 Hz, 2H).

b) (2S,4R)-4-[2-Chloro-4-((S)-2,2,2-trifluoro-1-methyl-ethoxy)-benzenesulfonyl]-1-(1-tri-fluoromethyl-cyclopropanecarbonyl)-pyrrolidine-2-carboxylic acid (1-cyano-cyclopropyl)-amide Step 1: (2S,4R)-4-[2-Chloro-4-((S)-2,2,2-trifluoro-1-methyl-ethoxy)-phenylsulfanyl]-1-(1-trifluoromethyl-cyclopropanecarbonyl)-pyrrolidine-2-carboxylic acid (1-cyano-cyclopropyl)-amide

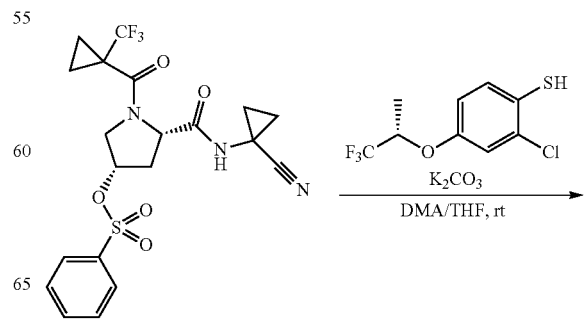

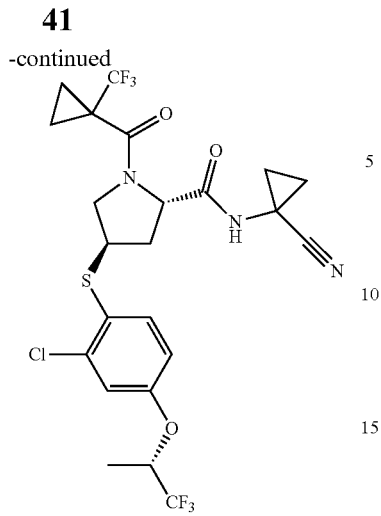
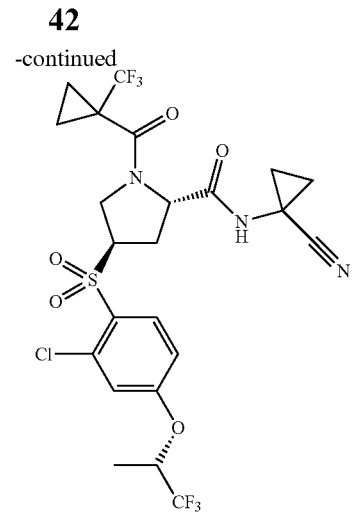

Benzenesulfonic acid (3S,5S)-5-(1-cyano-cyclopropylcarbamoyl)-1-(1-trifluoromethyl-cyclopropanecarbonyl)-pyrrolidin-3-yl ester (225 g, 477 mmol) was dissolved in dimethylacetamide (1.125 L) and potassium carbonate (166.5 g, 1.193 mol) was added. At room temperature, a solution of 2-chloro-4-((S)-2,2,2-trifluoro-1-methyl-ethoxy)-benzenethiol (142 g, 553.2 mmol) in tetrahydrofuran (135 mL) was added slowly, keeping the internal temperature below 29° C. (ice bath cooling necessary). The mixture was stirred for 5.5 h at room temperature. After addition of ice (700 g) and water (2 L), the mixture was extracted with tert-butyl-methylether (1×1.5 L, 3×750 mL). The combined organic extracts were washed with brine (450 mL) and concentrated in vacuo to yield the title compound as a brown viscous oil (300.4 g). The crude product (containing dimethylacetamide) was used in the next step without further purification.

Step 2: (2S,4R)-4-[2-Chloro-4-((S)-2,2,2-trifluoro-1-methyl-ethoxy)-benzenesulfonyl]-1-(1-trifluoromethyl-cyclopropanecarbonyl)-pyrrolidine-2-carboxylic acid (1-cyano-cyclopropyl)-amide

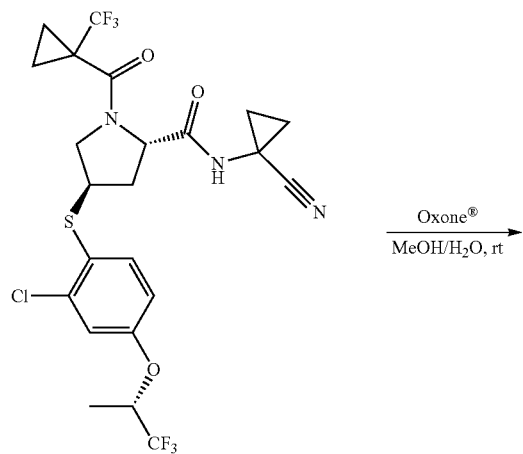

Oxone® (1.5 kg, 2.44 mol) was suspended in methanol (1.225 L) and water (385 mL) and a solution of (2S,4R)-4-[2-chloro-4-((S)-2,2,2-trifluoro-1-methyl-ethoxy)-phenylsulfanyl]-1-(1-trifluoromethyl-cyclopropanecarbonyl)-pyrrolidine-2-carboxylic acid (1-cyano-cyclopropyl)-amide (crude product, containing dimethylacetamide, 90.5% purity m/m, 300.4 g, 477.2 mmol) in methanol (800 mL) was added at a reaction temperature of 10-18° C. (ice bath cooling necessary). The mixture was stirred for 20 h at room temperature. The suspension was filtered and the remaining solid was washed with methanol (900 mL). Water (900 mL) was added to the filtrate and methanol was distilled off in vacuo. The resulting solution was extracted with tert-butyl-methylether (2×900 mL). The combined organic extracts were washed with a solution of sodium metabisulfite (40.0 g, 206 mmol) in water (450 mL), a potassium hydrogencarbonate solution (1M in water, 450 mL), and brine (450 mL). After drying over sodium sulfate, silica gel (300 g) was added. The resulting suspension was filtered and the remaining silica gel was washed with tert-butyl-methylether (900 mL). The combined filtrates were concentrated in vacuo and azeotroped with methanol (2×500 mL). The crude product (white foam, 270 g) was dissolved in methanol (450 mL) and added to water (4 L) with vigorous stirring. The suspension was stirred for 18 h at room temperature, filtered and the solid was washed with water (900 mL) and heptane (900 mL). After drying in vacuo, the title compound was obtained as an amorphous white solid (259 g, 97.6% purity by HPLC, 88% over 2 steps). MS (ESI & APCI): m/z=602.1 [M+H]$^+$, 619.1 [M+NH$_4$]$^+$. $^1$H NMR (CDCl$_3$, 400 MHz): δ1.11-1.21 (m, 2H), 1.30-1.43 (m, 1H), 1.35-1.40 (m, 1H), 1.42-1.47 (m, 1H), 1.49-1.56 (m, 3H), 1.57 (d, J=7.1 Hz, 3H), 2.16-2.23 (m, 1H), 2.86 (ddd, J=5.6 Hz, 8.3 Hz, 14.2 Hz, 1H), 3.85 (dd, J=7.5 Hz, 13.6 Hz, 1H), 4.34-4.39 (m, 1H), 4.72 (br d, J=13.3 Hz, 1H), 4.76-4.84 (m, 2H), 7.02 (dd, J=2.5 Hz, 9.0 Hz, 1H), 7.18 (d, J=2.5 Hz, 1H), 7.60 (s, 1H), 8.00 (d, J=8.9 Hz, 1H).

C2. Preparation of (2S,4R)-1-(1-methyl-cyclopropanecarbonyl)-4-[4-(2,2,2-trifluoro-ethoxy)-2-trifluoromethyl-benzenesulfonyl]-pyrrolidine-2-carboxylic acid (1-cyano-cyclopropyl)-amide a1) Benzenesulfonic acid (3S,5S)-5-(1-cyano-cyclopropylcarbamoyl)-1-(1-methyl-cyclopropanecarbonyl)-pyrrolidin-3-yl ester

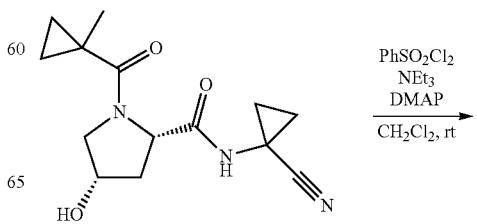

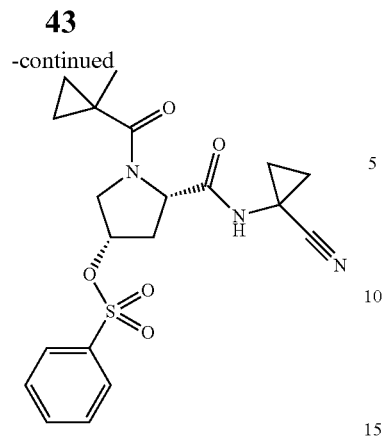

(2S,4S)-4-Hydroxy-1-(1-methyl-cyclopropanecarbonyl)-pyrrolidine-2-carboxylic acid (1-cyano-cyclopropyl)-amide (62.0 g, 224 mmol) and 4-(dimethylamino)pyridine (98%, 1.5 g, 12.0 mmol) were dissolved in dichloromethane (370 mL), benzenesulfonyl chloride (31.1 mL, 242 mmol), followed by triethylamine (49.8 mL, 358 mmol) were added at room temperature and the mixture was stirred for 16 h. After that, it was diluted with water (140 mL) and acidified by addition of hydrochloric acid (25% m/m, 21.4 mL). The phases were separated and the organic layer was washed with water (160 mL). The combined aqueous phases were extracted with dichloromethane (160 mL), the combined organic extracts were concentrated in vacuo to a volume of 430 mL. The solvent was exchanged via continuous distillation in vacuo (internal temperature 40° C., 670-170 mbar) to ethanol (670 mL added), the overall volume was kept constant (430 mL). The resulting solution was allowed to cool to room temperature and seed crystals (ca. 10 mg) were added to initiate crystallization. After crystallization had started, the suspension was stirred for 30 min at room temperature, heptane (430 mL) was added within 50 min and it was stirred for 12 h. The suspension was then filtered, the precipitate was washed with heptane/ethanol 2:1 (v/v, 321 mL) and heptane (107 mL) and dried in vacuo at 40° C. to yield the title compound as a white crystalline solid (80.0 g, 85%). MS (ESI & APCI): m/z=418.1 [M+H]+. 1H NMR (CDCl3, 600 MHz): δ 0.59-0.64 (m, 1H), 0.65-0.69 (m, 1H), 0.80-0.90 (m, 1H), 0.99-1.05 (m, 1H), 1.12-1.21 (m, 2H), 1.30 (s, 3H), 1.47-1.53 (m, 2H), 2.15 (ddd, J=5.8 Hz, 9.2 Hz, 14.6 Hz, 1H), 2.70 (br d, J=14.0 Hz, 1H), 3.83 (dd, J=3.8 Hz, 12.3 Hz, 1H), 4.08 (dd, J=5.3 Hz, 12.4 Hz, 1H), 4.55 (br s, 1H), 5.04-5.08 (m, 1H), 7.49 (br s, 1H), 7.61 (t, J=7.8 Hz, 2H), 7.70 (t, J=7.5 Hz, 1H), 7.96 (d, J=7.6 Hz, 2H).

b1) (2S,4R)-1-(1-Methyl-cyclopropanecarbonyl)-4-[4-(2,2,2-trifluoro-ethoxy)-2-trifluoromethyl-phenylsulfanyl]-pyrrolidine-2-carboxylic acid (1-cyano-cyclopropyl)-amide

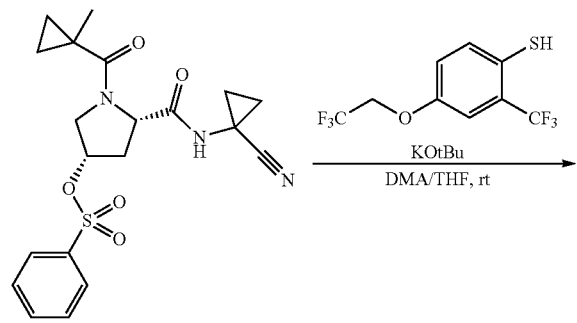

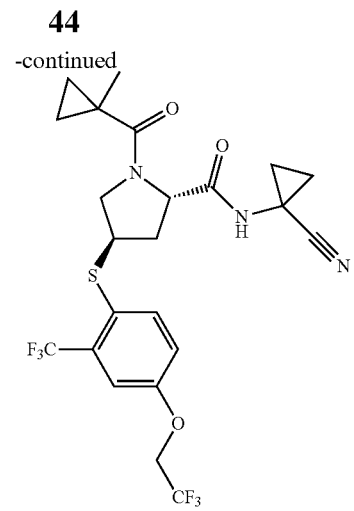

A solution of 4-(2,2,2-trifluoro-ethoxy)-2-trifluoromethyl-benzenethiol (56.1 g, 196 mmol) in tetrahydrofuran (93 mL) was added at room temperature to a suspension of potassium tert-butoxide (22.8 g, 203 mmol) in tetrahydrofuran (370 mL). The orange-brown clear solution was stirred for 20 min and a solution of benzenesulfonic acid (3S,5S)-5-(1-cyano-cyclopropylcarbamoyl)-1-(1-methyl-cyclopropanecarbonyl)-pyrrolidin-3-yl ester (74.4 g, 178 mmol) in dimethylacetamide (240 mL) was added. The mixture was stirred for 15 h at room temperature. Water (550 mL) and ethyl acetate (500 mL) were added and phases were separated. The aqueous layer was extracted with ethyl acetate (500 mL), the combined organic solution of 4-(2,2,2-trifluoro-eth sodium chloride (124 g) in water (1.1 L) (2×600 mL) and concentrated in vacuo to a volume of ca. 260 mL. Toluene (600 mL) was added, the mixture again concentrated in vacuo to a volume of ca. 260 mL and further toluene (240 mL) was added. The warm mixture (internal temperature 45° C.) was filtered, the precipitate was washed with toluene (120 mL) and the combined filtrate was allowed to slowly cool to room temperature (within 60 min). Crystallization started at 26° C. internal temperature. The suspension was stirred for 1 h at 22° C., heptane (620 mL) was added within 45 min and the suspension was stirred for 17 h at room temperature before it was filtered. The precipitate was washed with toluene/heptane 1:1 (v/v, 240 mL) and heptane (120 mL) and dried in vacuo at 40° C. to provide the title compound as off-white crystals (87.7 g, 96.1% purity, 88%). MS (ESI & APCI): m/z=536.1 [M+H]+. 1H NMR (CDCl3, 600 MHz): δ0.58-0.62 (m, 1H), 0.64-0.68 (m, 1H), 0.89-0.93 (m, 1H), 1.04-1.09 (m, 1H), 1.16-1.22 (m, 2H), 1.31 (s, 3H), 1.45-1.55 (m, 2H), 1.88-1.94 (m, 1H), 2.79-2.85 (m, 1H), 3.83-3.88 (m, 1H), 3.91-3.98 (m, 2H), 4.41 (q, J=7.9 Hz, 2H), 4.61 (dd, J=4.7 Hz, 8.0 Hz, 1H), 7.12 (dd, J=2.9 Hz, 8.6 Hz, 1H), 7.31 (d, J=2.8 Hz, 1H), 7.61 (d, J=8.6 Hz, 1H), 8.04 (br s, 1H).

b2) (2S,4R)-1-(1-Methyl-cyclopropanecarbonyl)-4-[4-(2,2,2-trifluoro-ethoxy)-2-trifluoromethyl-phenylsulfanyl]-pyrrolidine-2-carboxylic acid (1-cyano-cyclopropyl)-amide c1) (2S,4R)-1-(1-Methyl-cyclopropanecarbonyl)-4-[4-(2,2,2-trifluoro-ethoxy)-2-trifluoromethyl-benzenesulfonyl]-pyrrolidine-2-carboxylic acid (1-cyano-cyclopropyl)-amide

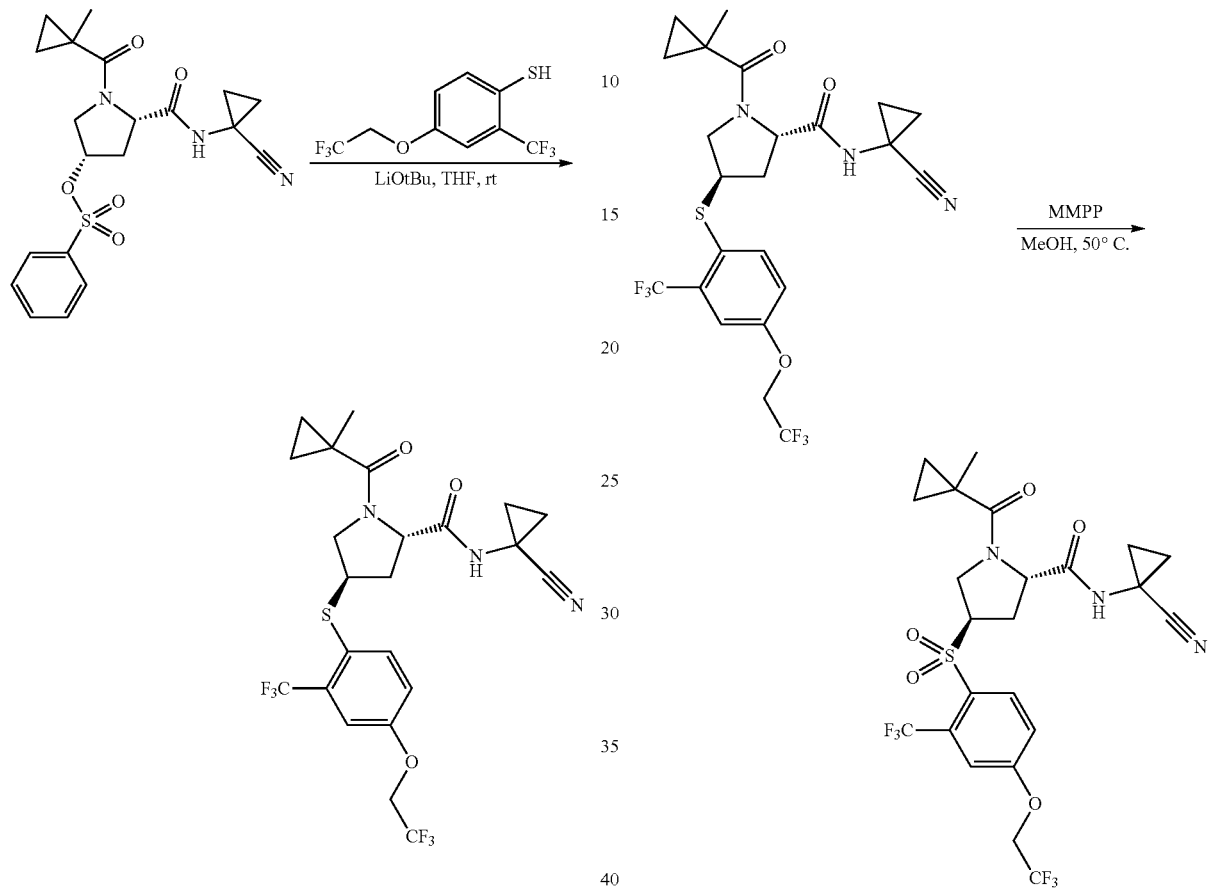

To a stirred suspension of 4-(2,2,2-trifluoro-ethoxy)-2-trifluoromethyl-benzenethiol (30.4 g, 110 mmol) and benzenesulfonate (3S,5S)-5-(1-cyano-cyclopropylcarbamoyl)-1-(1-methyl-cyclopropanecarbonyl)-pyrrolidin-3-yl ester (41.7 g, 100 mmol) in THF (50 mL) was added at room temperature 20% lithium tert-butoxide in THF (44.0 g≅49.5 mL, 110 mmol) over 40 min. After stirring at room temperature for 18 h, the reaction mixture was hydrolyzed with deionized water (400 mL) and extracted twice with ethyl acetate (400 mL & 200 mL). Both organic layers were washed with 10% brine (200 mL), combined, dried over $Na_2SO_4$, and filtered. Evaporation of the solvent and careful drying (45° C./≥10 mbar) gave 56.3 g crude product as voluminous, off-white foam, which was dissolved in 250 mL toluene at 50° C. The crystallization, which started during cooling, was completed after stirring at room temperature for 1 h by the dropwise addition of 200 mL heptane (note 11), followed by stirring at room temperature for 20 h. Filtration and drying (50° C./10 mbar/3 days for removal of toluene to ~1%) yielded 51.2 g (95.7%) title product as an off-white crystalline powder, mp. 66-76° C. $[\alpha]_D^{20}$=−67.5 (c 1.0; $CHCl_3$). $^1$H NMR ($CDCl_3$, 400 MHz) δ0.55-0.70 (m, 2H), 0.87-0.95 (m, 1H), 1.02-1.10 (m, 1H), 1.13-1.23 (m, 2H), 1.31 (s, 3H), 1.42-1.55 (m, 2H), 1.85-1.97 (m, 1H), 2.74-2.85 (m, 1H), 3.80-4.00 (m, 3H), 4.40 (q, J=7.8 Hz, 2H), 4.60 (dd, $J_1$=8.1 Hz, $J_2$=4.6 Hz, 1H), 7.11 (dd, $J_1$=8.6 Hz, $J_2$=2.7 Hz, 1H), 7.30 (d, J=3.0 Hz, 1H), 7.61 (d, J=8.6 Hz, 1H), 8.05 (s, 1H).

To a solution of magnesium monoperoxyphthalate hexahydrate (11.8 g, 20 mmol, assay 84%) in methanol (100 mL) was added under stirring a solution of (2S,4R)-4-[2-chloro-4-(2,2,2-trifluoro-ethoxy)-phenylsulfanyl]-1-(1-methyl-cyclo-propanecarbonyl)-pyrrolidine-2-carboxylic acid (1-cyano-cyclopropyl)-amide (10.7 g, 20 mmol) in methanol (30 mL) over 15 min. After stirring at 50° C. for 8 h, additional magnesium monoperoxyphthalate hexahydrate (13.0 g, 22 mmol) was added all at once and the white suspension was stirred for further 16 h. The reaction mixture was cooled to room temperature and the excess magnesium monoperoxyphthalate was destroyed by dropwise addition of 39% aqueous sodium bisulfite (~9 mL). After removal of the main part of the methanol by rotary evaporation (45° C./≥80 mbar), dichloromethane (100 mL) was added to the white slurry and the mixture was carefully neutralized under stirring to pH 7 by the addition of 1 M NaOH (~95 mL). The organic layer was washed with 5% $NaHCO_3$ (50 mL) and both aqueous layers were extracted with dichloromethane (50 mL). The combined organic layers were dried ($Na_2SO_4$), filtered, and evaporated (40° C./≥10 mbar), affording a white voluminous foam (11.51 g) which was dissolved in isopropanol (50 mL) at ~60° C. Deionized water (100 mL) was added under stirring over 30 min and the resulting white suspension was stirred at room temperature for 3 h and filtered to yield after washing with isopropanol-water 1:2 (~20 mL) and drying (50° C./10 mbar/4 h) the title product (10.6 g, 93.3%) as a white crystalline powder, mp. 125.5-129.5° C. $[\alpha]_D^{20}=-75.1$ (c 1.0; CHCl$_3$). $^1$H NMR (CDCl$_3$, 400 MHz) δ 0.59-0.80 (m, 2H), 1.04-1.24 (m, 4H), 1.36 (s, 3H), 1.44-1.56 (m, 2H), 2.21 (m, 1H), 2.73 (m, 1H), 3.88 (dd, J$_1$=12.5 Hz, J$_2$=7.5 Hz, 1H), 4.16 (m, 1H), 4.51 (q, J=7.8 Hz, 2H), 4.69 (dd, J$_1$=12.5 Hz, J$_2$=4.0 Hz, 1H), 4.75 (dd, J$_1$=8.3 Hz, J$_2$=5.1 Hz, 1H), 7.25 (dd, J$_1$=9.0 Hz, J$_2$=2.7 Hz, 1H), 7.53 (d, J=2.7 Hz, 1H), 7.97 (s, 1H), 8.19 (d, J=9.0 Hz, 1H). ESI-MS (m/z) [M+H]$^+$ (100).

c2) (2S,4R)-1-(1-Methyl-cyclopropanecarbonyl)-4-[4-(2,2,2-trifluoro-ethoxy)-2-trifluoromethyl-benzenesulfonyl]-pyrrolidine-2-carboxylic acid (1-cyano-cyclopropyl)-amide

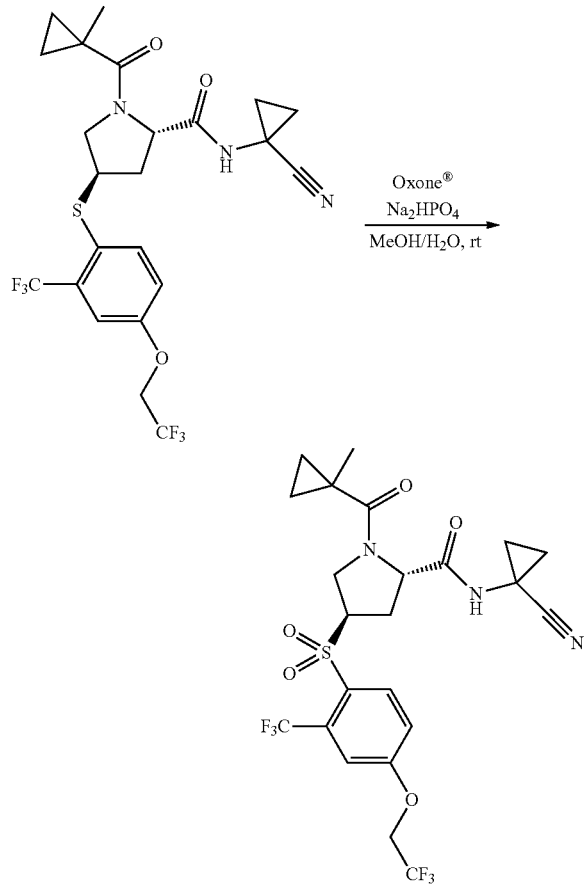

Oxone® (264.6 g, 430 mmol) and disodium hydrogenphosphate (457.2 g, 2.72 mol) were suspended in methanol (570 mL) and water (810 mL) and a solution of (2S,4R)-1-(1-methyl-cyclopropanecarbonyl)-4-[4-(2,2,2-trifluoro-ethoxy)-2-trifluoromethyl-phenylsulfanyl]-pyrrolidine-2-carboxylic acid (1-cyano-cyclopropyl)-amide (90.0 g, 168 mmol) in methanol (600 mL) was added at room temperature within 30 min. The mixture was stirred for 90 h at room temperature. The suspension was warmed to 40° C., filtered and the filtered solid was washed with methanol (1000 mL). The combined filtrate was concentrated in vacuo to a volume of 1.1 L and dichloromethane (900 mL) was added. After phase separation, the aqueous layer was extracted with dichloromethane (450 mL), the combined organic extracts were washed with a solution of sodium thiosulfate (26.6 g, 168 mmol) in water (900 mL) and water (900 mL), filtered, and concentrated in vacuo to a volume of ca. 220 mL. Isopropanol (900 mL) was then added and the solution was concentrated in vacuo to a volume of ca. 500 mL. Water (500 mL) was added at 50° C. and the solution was allowed to cool to room temperature (crystallization started). Additional water (500 mL) was added slowly and the crystal suspension was stirred for 5 h at room temperature. The suspension was filtered, the precipitate was washed with water/isopropanol 2:1 (v/v, 270 mL) and water (270 mL) and dried in vacuo at 50° C. to yield the title compound as colorless crystals (87.0 g, 91%). mp. 126.0-127.0° C. MS (ESI & APCI): m/z=568.1 [M+H]$^+$. $^1$H NMR (CDCl$_3$, 600 MHz): δ 0.62-0.66 (m, 1H), 0.73-0.78 (m, 1H), 1.07-1.14 (m, 2H), 1.15-1.21 (m, 2H), 1.36 (s, 3H), 1.46-1.54 (m, 2H), 2.21 (ddd, J=5.4 Hz, 8.4 Hz, 13.8 Hz, 1H), 2.71-2.77 (m, 1H), 3.89 (dd, J=7.5 Hz, 12.4 Hz, 1H), 4.13-4.19 (m, 1H), 4.51 (q, J=7.7 Hz, 2H), 4.69 (dd, J=3.8 Hz, 12.4 Hz, 1H), 4.75 (dd, J=5.1 Hz, 8.3 Hz, 1H), 7.25 (dd, J=2.7 Hz, 8.9 Hz, 1H), 7.53 (d, J=2.6 Hz, 1H), 7.97 (br s, 1H), 8.19 (d, J=8.8 Hz, 1H). Anal. Calcd for C23H23F6N3O5S: C, 48.68; H, 4.08; N, 7.40; S, 5.65; F, 20.09. Found: C, 48.59; H, 4.05; N, 7.53; S, 5.76; F, 20.08.

C3. Preparation of (2S,4R)-4-[4-(2-methyl-pyridin-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide Step 1: (2S,4R)-4-[4-(2-Methyl-pyridin-4-yl)-2-trifluoromethyl-phenylsulfanyl]-1-(1-trifluoromethyl-cyclopropanecarbonyl)-pyrrolidine-2-carboxylic acid (1-cyano-cyclopropyl)-amide

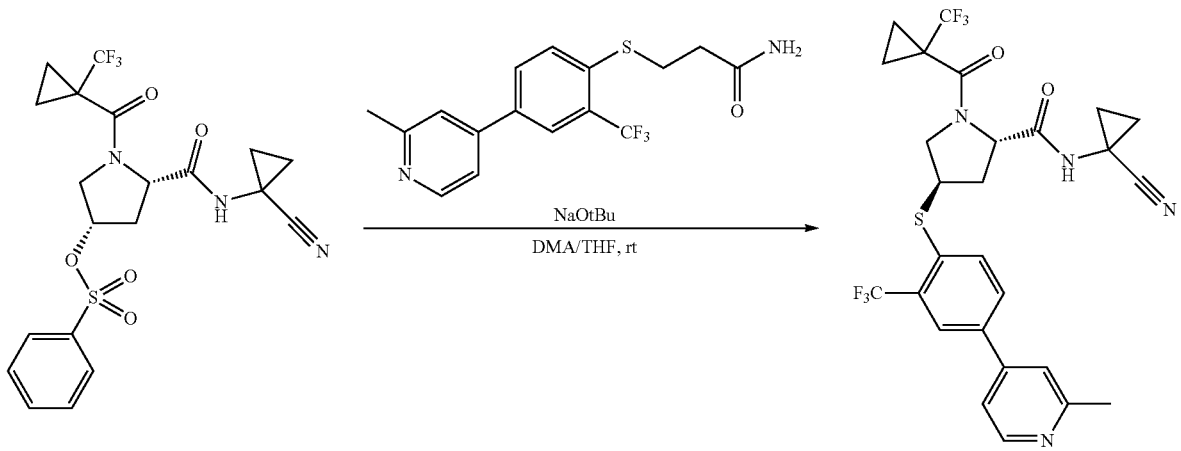 [SMILES: N#CC1(NC(=O)[C@@H]2C[C@H](OS(=O)(=O)c3ccccc3)CN2C(=O)C2(C(F)(F)F)CC2)CC1 ; Cc1cc(-c2ccc(SCCC(N)=O)c(C(F)(F)F)c2)ccn1 ; Cc1cc(-c2ccc(S[C@@H]3C[C@@H](C(=O)NC4(C#N)CC4)N(C(=O)C4(C(F)(F)F)CC4)C3)c(C(F)(F)F)c2)ccn1 ; "NaOtBu"]

3-[4-(2-Methyl-pyridin-4-yl)-2-trifluoromethyl-phenyl-sulfanyl]-propionamide (200 g, 588 mmol) was dissolved in tetrahydrofuran (1.0 L) before sodium tert-butoxide (55.5 g, 578 mmol) was added and the fine suspension was stirred for 2 h at room temperature. N,N-dimethylacetamide (500 mL) was added and the solution was stirred for further 1.5 h. A solution of benzenesulfonic acid (3S,5S)-5-(1-cyano-cyclopropylcarbamoyl)-1-(1-trifluoromethyl-cyclopropanecarbonyl)-pyrrolidin-3-yl ester (237.5 g, 504 mmol) in N,N-dimethylacetamide (500 mL) was added and the brown, clear solution was stirred for 40 h. The mixture was diluted with water (3 L) and extracted with tert-butyl methyl ether (1×2 L, 3×1 L). The combined organic extracts were washed with an aqueous sodium carbonate solution (1 M, 1.0 L) and brine (1.0 L), dried over sodium sulfate, and concentrated in vacuo to yield the title compound as a brown gum (327.8 g). The crude product (containing dimethylacetamide) was used in the next step without further purification. For characterization purposes, a 4 g sample of crude material was purified by filtration over silica gel (20 g, eluent: ethyl acetate (200 mL)). 3.3 g of purified material were obtained as an off-white solid. MS (EI): m/z=583.1 [M+H]$^+$. $^1$H NMR (CDCl$_3$, 300 MHz): δ 1.10-1.36 (m, 6H), 1.49-1.58 (m, 2H), 1.99-2.12 (m, 1H), 2.65 (s, 3H), 2.90-3.02 (m, 1H), 3.92 & 4.02 (ABX, J$_{AB}$=11.9 Hz, J$_{AX}$=4.8 Hz, J$_{BX}$=5.8 Hz, each 1H), 4.12-4.22 (m, 1H), 4.71 (dd, J=4.7 Hz, 7.8 Hz, 1H), 7.31 (d, J=5.3 Hz, 1H), 7.37 (br s, 1H), 7.60-7.69 (m, 2H), 7.80 (d, J=8.3 Hz, 1H), 7.93 (s, 1H), 8.60 (d, J=5.1 Hz, 1H).

Step 2: (2S,4R)-4-[4-(2-Methyl-pyridin-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide

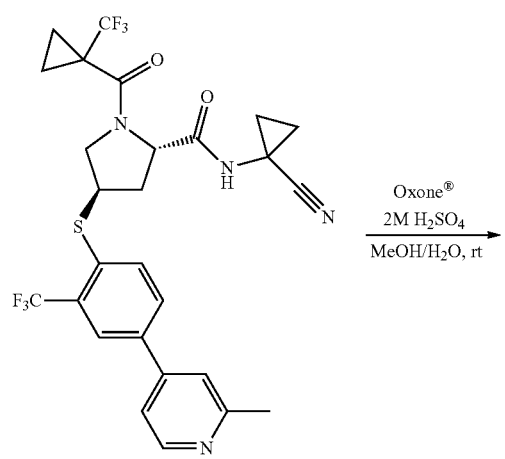

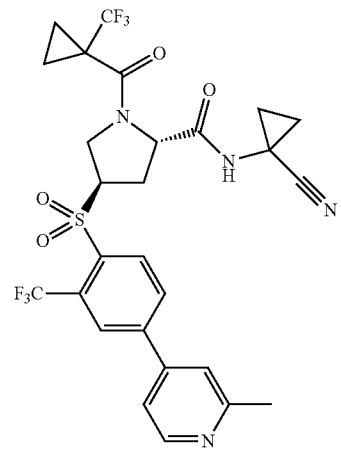

(2S,4R)-4-[4-(2-Methyl-pyridin-4-yl)-2-trifluoromethyl-phenylsulfanyl]-1-(1-trifluoromethyl-cyclopropanecarbonyl)-pyrrolidine-2-carboxylic acid (1-cyano-cyclopropyl)-amide (crude product, containing dimethylacetamide, 89.4% purity m/m, 327.8 g, 503 mmol) was dissolved in methanol (930 mL) and sulfuric acid (1 M in water, 3.7 L) at 0-5° C. (ice bath). Oxone® (980 g, 1590 mmol) was added in one portion (slightly exotherm) and the mixture was stirred for 20 h at room temperature. Celite (100 g) was then added, the mixture was filtered and the precipitate was washed with water/methanol (4:1 v/v, 500 mL). Sodium metabisulfite (183 g, 965 mmol) was added in small portions to the combined filtrate (exotherm). Ethyl acetate (1.5 L) was added and the biphasic mixture was basified to pH>8 by addition of an aqueous ammonia solution (25% m/m, 1.2 L). After phase separation, the aqueous layer was extracted with ethyl acetate (2×1.2 L), the combined organic extracts were washed with water/brine (1:1 v/v, 750 mL) and brine (750 mL), dried over sodium sulfate, and concentrated in vacuo at 55° C. The crude product was dissolved in dichloromethane/methanol (100:3 v/v, 1.45 L) and silica gel (500 g) was added. The slurry was filtered and washed with dichloromethane/methanol (100:3 v/v, 2.9 L). The combined filtrates were concentrated in vacuo at 55° C. The residue, a white foam (279.2 g), was dissolved in ethanol (1600 mL) at 70° C. before pre-warmed water (60-65° C., 800 mL) was added quickly and the resulting mixture was slowly cooled. The suspension was stirred for 20 h at room temperature, before it was filtered. The precipitate was washed with ethanol/water (1:1 v/v, 800 mL) and n-heptane (800 mL), and dried in vacuo at 55° C. to afford the title compound as colorless crystals (228.1 g, 74% over 2 steps). MS (ESI & APCI): m/z=615.1 [M+H]. $^1$H NMR (CDCl$_3$, 600 MHz): δ 1.11-1.22 (m, 2H), 1.32-1.42 (m, 2H), 1.46-1.57 (m, 4H), 2.24-2.30 (m, 1H), 2.69 (s, 3H), 2.86 (ddd, J=5.7 Hz, 8.0 Hz, 14.1 Hz, 1H), 3.88 (dd, J=7.1 Hz, 13.3 Hz, 1H), 4.14-4.19 (m, 1H), 4.83 (dd, J=1.7 Hz, 13.3 Hz, 1H), 4.88 (dd, J=5.6 Hz, 8.6 Hz, 1H), 7.35 (dd, J=1.4 Hz, 5.2 Hz, 1H), 7.40 (bs, 1H), 7.63 (bs, 1H), 8.01 (dd, J=1.8 Hz, 8.2 Hz, 1H), 8.17 (d, J=1.6 Hz, 1H), 8.29 (d, J=8.3 Hz, 1H), 8.68 (d, J=5.2 Hz, 1H).

C4. Preparation of (2S,4R)-4-[4-(1-methyl-1H-pyrazol-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide Process Variant 1

Step 1: (2S,4R)-4-[4-(1-Methyl-1H-pyrazol-4-yl)-2-trifluoromethyl-phenylsulfanyl]-1-(1-trifluoromethyl-cyclopropanecarbonyl)-pyrrolidine-2-carboxylic acid (1-cyano-cyclopropyl)-amide

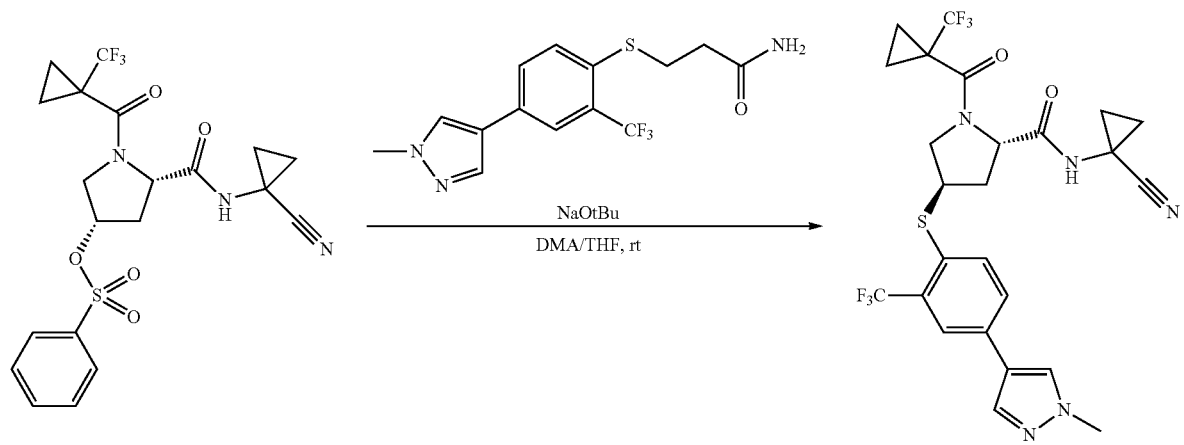 [SMILES: N#CC1(NC(=O)[C@@H]2C[C@H](OS(=O)(=O)c3ccccc3)CN2C(=O)C2(C(F)(F)F)CC2)CC1 ; Cn1cc(-c2ccc(SCCC(N)=O)c(C(F)(F)F)c2)cn1 ; Cn1cc(-c2ccc(S[C@@H]3C[C@@H](C(=O)NC4(C#N)CC4)N(C(=O)C4(C(F)(F)F)CC4)C3)c(C(F)(F)F)c2)cn1 ; "NaOtBu"]

3-[4-(1-Methyl-1H-pyrazol-4-yl)-2-trifluoromethyl-phenylsulfanyl]-propionamide (16.3 g, 49.6 mmol) was dissolved in tetrahydrofuran (80 mL) before sodium tert-butoxide (4.7 g, 48.9 mmol) was added and the fine suspension was stirred for 2 h at room temperature. N,N-dimethylacetamide (40 mL) was added and the mixture was stirred for further 2.5 h at room temperature. A solution of benzenesulfonic acid (3S,5S)-5-(1-cyano-cyclopropylcarbamoyl)-1-(1-trifluoromethyl-cyclopropanecarbonyl)-pyrrolidin-3-yl ester (20 g, 42.4 mmol) in N,N-dimethylacetamide (40 mL) was added and the yellow, fine suspension was stirred for 42 h at room temperature. The mixture was diluted with water (240 mL) and extracted with tert-butyl methyl ether (1×160 mL, 3×80 mL). The combined organic extracts were washed with an aqueous sodium carbonate solution (1 M, 80 mL) and brine (80 mL), dried over sodium sulfate and concentrated in vacuo to yield the title compound as a light brown foam (27.1 g). The crude product (containing dimethylacetamide) was used in the next step without further purification. For characterization purposes, a 2 g sample of crude material was purified by column chromagraphy on silica gel (eluent: gradient ethyl acetate/heptane 4:1 (v/v) to ethyl acetate). Likewise, 1.7 g of purified material were obtained. MS (ESI & APCI): m/z=572.1 [M+H]$^+$, 589.2 [M+NH$_4$]$^+$. $^1$H NMR (CDCl$_3$, 600 MHz): δ 1.12-1.22 (m, 3H), 1.28-1.34 (m, 3H), 1.49-1.54 (m, 2H), 2.02 (ddd, J=5.6 Hz, 8.2 Hz, 13.6 Hz, 1H), 2.88 (ddd, J=5.7 Hz, 5.7 Hz, 13.7 Hz, 1H), 3.89-3.99 (m, 2H), 3.97 (s, 3H), 4.04-4.09 (m, 1H), 4.69 (dd, J=5.2 Hz, 8.2 Hz, 1H), 7.55 (d, J=8.2 Hz, 1H), 7.60 (bs, 1H), 7.62 (dd, J=1.8 Hz, 8.2 Hz, 1H), 7.69 (s, 1H), 7.77 (d, J=1.8 Hz, 1H), 7.79 (s, 1H).

Step 2: (2S,4R)-4-[4-(1-Methyl-1H-pyrazol-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide

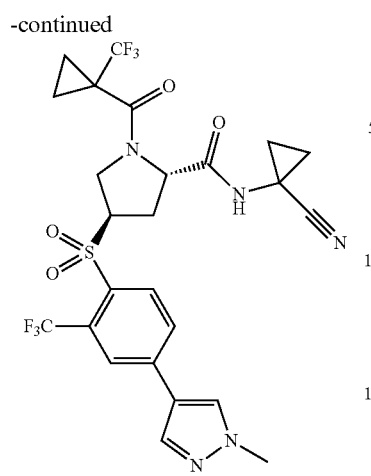

Oxone® (53.0 g, 86.2 mmol) and disodium hydrogenphosphate (13.0 g, 91.4 mmol) were suspended in methanol (45 mL) and water (16 mL) and a solution of (2S,4R)-4-[4-(1-methyl-1H-pyrazol-4-yl)-2-trifluoromethyl-phenylsulfanyl]-1-(1-trifluoromethyl-cyclopropanecarbonyl)-pyrrolidine-2-carboxylic acid (1-cyano-cyclopropyl)-amide (crude product, containing dimethylacetamide, 89.3% purity m/m, 11.2 g, 17.5 mmol) in methanol (30 mL) was added at 5-15° C. internal temperature within 15 min. The bright yellow suspension was stirred for 20 h at room temperature. After filtration, the remaining solid was washed with methanol (50 mL). Water (30 mL) was added to the combined filtrate before methanol was distilled off in vacuo. The aqueous residue was extracted with ethyl acetate (3×20 mL). The combined organic extracts were washed subsequently with a solution of sodium metabisulfite (1.9 g, 10.0 mmol) in water (30 mL), a saturated aqueous sodium hydrogencarbonate solution (30 mL), and brine (30 mL), dried over sodium sulfate, and concentrated in vacuo. The residue was dissolved in dichloromethane/methanol (100:3 (vol/vol), 50 mL) and filtered over a plug of silica gel (20 g). The plug was washed with dichloromethane/methanol (100:3 vol/vol, 100 mL) and the combined filtrate was concentrated in vacuo. The crude product, a yellow foam (9.4 g), was dissolved in ethyl acetate (25 mL) and toluene (94 mL), concentrated in vacuo to a volume of ca. 80 mL, and stirred for 1.5 h at room temperature. The suspension was filtered and the remaining solid was washed with toluene (20 mL) and n-heptane (20 mL) and dried in vacuo. The resulting white crystalline material (7.15 g) was again dissolved in acetone (35 mL) and water (70 mL). The resulting emulsion was seeded and the suspension was stirred vigorously for 20 h at room temperature. After filtration, the precipitate was washed with acetone/water (1:4 (v/v), mL) and n-heptane (20 mL) and dried in vacuo to give the title compound as colorless crystals (6.03 g, 57% over 2 steps). MS (ESI & APCI): m/z=604.1 [M+H]⁺, 621.1 [M+NH₄]⁺. ¹H NMR (CDCl₃, 600 MHz): δ 1.10-1.22 (m, 2H), 1.30-1.35 (m, 1H), 1.35-1.41 (m, 1H), 1.45-1.59 (m, 4H), 2.22-2.28 (m, 1H), 2.84 (ddd, J=5.9 Hz, 8.0 Hz, 14.3 Hz, 1H), 3.84 (dd, J=7.1 Hz, 13.2 Hz, 1H), 4.00 (s, 3H), 4.08-4.14 (m, 1H), 4.81 (d, J=13.3 Hz, 1H), 4.86 (dd, J=5.8 Hz, 8.6 Hz, 1H), 7.65 (bs, 1H), 7.80-7.83 (m, 2H), 7.89 (s, 1H), 7.99 (d, J=1.6 Hz, 1H), 8.12 (d, J=8.4 Hz, 1H).

Process Variant 2

Step 1: (2S,4R)-4-[4-(1-Methyl-1H-pyrazol-4-yl)-2-trifluoromethyl-phenylsulfanyl]-1-(1-trifluoromethyl-cyclopropanecarbonyl)-pyrrolidine-2-carboxylic acid (1-cyano-cyclopropyl)-amide

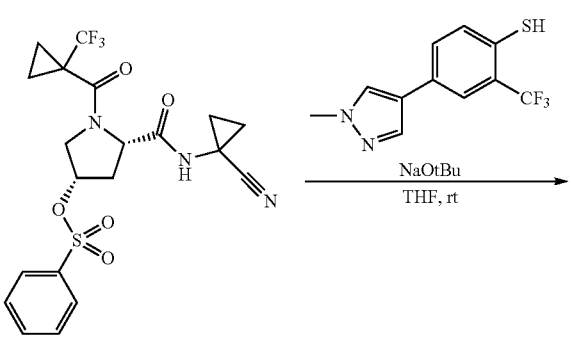

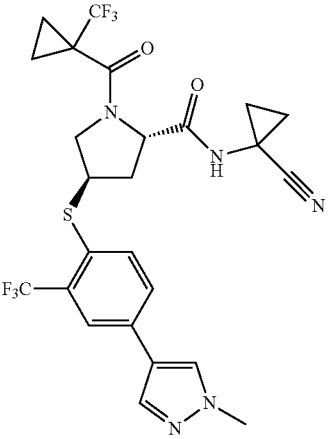

(3S,5S)-5-(1-Cyano-cyclopropylcarbamoyl)-1-(1-trifluoromethyl-cyclopropanecarbonyl)-pyrrolidin-3-yl ester (52.4 g, 111 mmol) and 4-(1-methyl-1H-pyrazol-4-yl)-2-trifluoromethyl-benzenethiol (32.4 g, 122 mmol) were dissolved in tetrahydrofuran (250 mL). A solution of sodium tert-butoxide in tetrahydrofuran (25% w/w, 44.8 g, 49.2 mL, 116 mmol) was added at internal temperature of 20° C.-28° C. within 20 min. The mixture was stirred for 18 h at room temperature. After that, a solution of sodium chloride in water (10% w/w, 250 mL) and 2-methyltetrahydrofuran (250 mL) were added. The phases were separated, the organic layer was washed with a solution of sodium chloride in water (10% w/w, 250 mL) and concentrated in vacuo. The crude product was dissolved in acetonitrile (250 mL), concentrated in vacuo, redissolved again in acetonitrile (250 mL) and filtered over charcoal to remove inorganic salts. The filtered material was washed with acetonitrile (100 ml) and the combined filtrates were concentrated in vacuo to yield crude title compound as a foam that was used in the next step without further purification (64.0 g, 97.6% purity by HPLC, 98.3%).

Step 2: (2S,4R)-4-[4-(1-Methyl-1H-pyrazol-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide

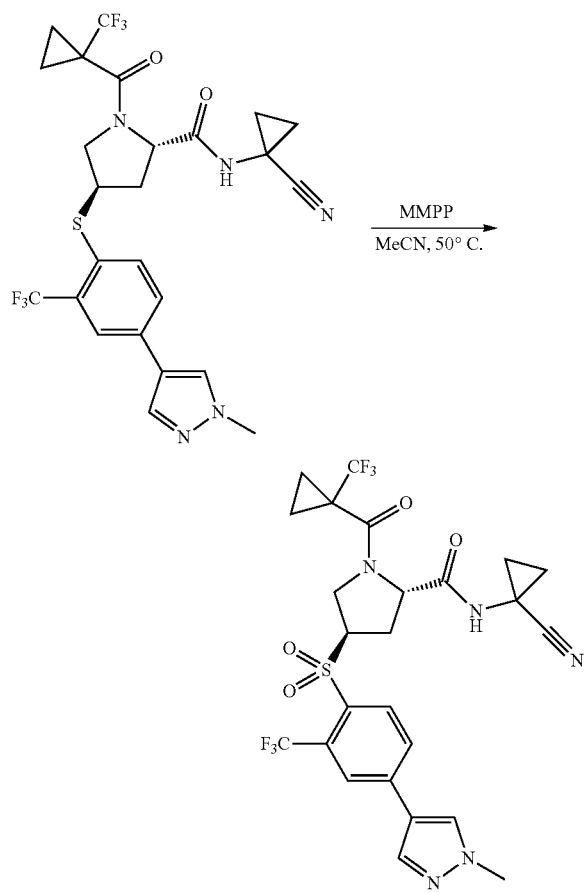

(2S,4R)-4-[4-(1-Methyl-1H-pyrazol-4-yl)-2-trifluoromethyl-phenylsulfanyl]-1-(1-trifluoromethyl-cyclopropanecarbonyl)-pyrrolidine-2-carboxylic acid (1-cyano-cyclopropyl)-amide (crude product, 97.6% purity, 64.0 g, 109 mmol) was dissolved in acetonitrile (480 mL) and magnesium monoperoxyphthalate hexahydrate (76.0 g, 154 mmol) was added. The resulting white suspension was stirred for 5 h at 50° C. After that, a suspension of magnesium monoperoxyphthalate hexahydrate (76.0 g, 154 mmol) in acetonitrile (150 mL) was added and the mixture was stirred for further 16 h at 50° C. After cooling to 20° C., water (480 mL) and a solution of sodium metabisulfite in water (40% w/w, 56.8 mL, 109 mmol) were added. The mixture was basified to pH 8 by addition of an aqueous sodium hydroxide solution (3 M, ca. 290 mL), extracted with dichloromethane (1 L), the organic phase was washed with saturated aqueous sodium hydrogencarbonate solution (1 L) and concentrated in vacuo. The residue was dissolved in dichloromethane (300 mL) and filtered to remove solid impurities. The solvent of the filtrate was exchanged to ethanol by continuous distillation while keeping the volume constant (ca. 750 mL ethanol used). The desired product started to crystallize. The resulting suspension was stirred for 12 h at 0° C., filtered, the precipitate was washed with cold ethanol (50 mL) and dried in vacuo at 45° C. to obtain the title compound as white crystals (50.0 g, 74.9%). MS (ESI & APCI): m/z=604.1 [M+H]$^+$, 621.1 [M+NH$_4$]$^+$. $^1$H NMR (CDCl$_3$, 600 MHz): δ 1.10-1.22 (m, 2H), 1.30-1.35 (m, 1H), 1.35-1.41 (m, 1H), 1.45-1.59 (m, 4H), 2.22-2.28 (m, 1H), 2.84 (ddd, J=5.9 Hz, 8.0 Hz, 14.3 Hz, 1H), 3.84 (dd, J=7.1 Hz, 13.2 Hz, 1H), 4.00 (s, 3H), 4.08-4.14 (m, 1H), 4.81 (d, J=13.3 Hz, 1H), 4.86 (dd, J=5.8 Hz, 8.6 Hz, 1H), 7.65 (bs, 1H), 7.80-7.83 (m, 2H), 7.89 (s, 1H), 7.99 (d, J=1.6 Hz, 1H), 8.12 (d, J=8.4 Hz, 1H).

C5. Preparation of (2S,4R)-1-(1-methyl-cyclopropanecarbonyl)-4-[4-(2-methyl-pyridin-4-yl)-2-trifluoromethyl-benzenesulfonyl]-pyrrolidine-2-carboxylic acid (1-cyano-cyclo-propyl)-amide Step 1: (2S,4R)-1-(1-Methyl-cyclopropanecarbonyl)-4-[4-(2-methyl-pyridin-4-yl)-2-trifluoromethyl-phenylsulfanyl]-pyrrolidine-2-carboxylic acid (1-cyano-cyclopropyl)-amide

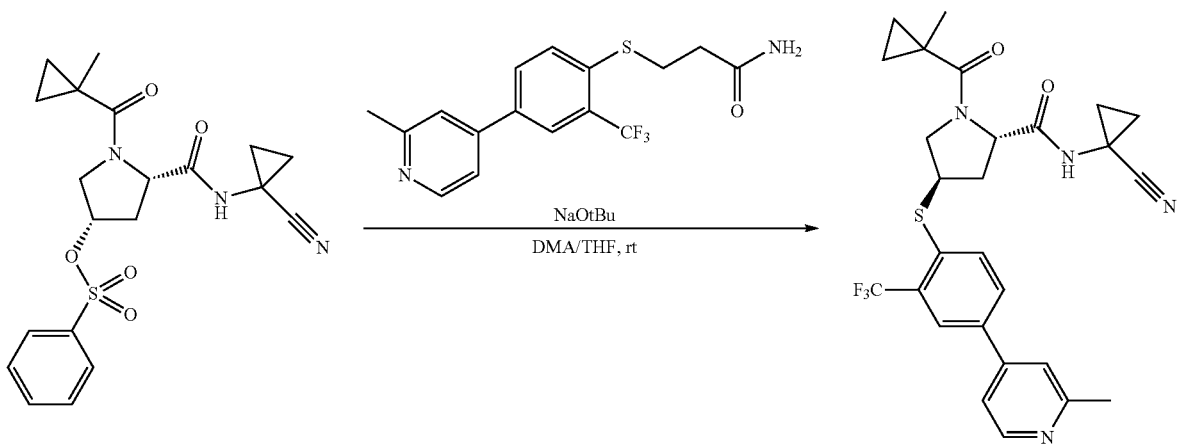 [SMILES: CC1(C(=O)N2C[C@@H](OS(=O)(=O)c3ccccc3)C[C@H]2C(=O)NC2(C#N)CC2)CC1 ; Cc1cc(-c2ccc(SCCC(N)=O)c(C(F)(F)F)c2)ccn1 ; Cc1cc(-c2ccc(S[C@@H]3C[C@@H](C(=O)NC4(C#N)CC4)N(C(=O)C4(C)CC4)C3)c(C(F)(F)F)c2)ccn1 ; "NaOtBu"]

3-[4-(2-Methyl-pyridin-4-yl)-2-trifluoromethyl-phenyl-sulfanyl]-propionamide (15.0 g, 44.1 mmol) was dissolved in tetrahydrofuran (75 mL), before sodium tert-butoxide (4.15 g, 43.2 mmol) was added and the fine suspension was stirred for 2 h at room temperature. N,N-dimethylacetamide (37 mL) was added and the solution was stirred for further 2 h. A solution of benzenesulfonic acid (3S,5S)-5-(1-cyano-cyclopropylcarbamoyl)-1-(1-methyl-cyclo-propanecarbonyl)-pyrrolidin-3-yl ester (15.7 g, 37.7 mmol) in N,N-dimethylacetamide (37 mL) was added and the brown, clear solution was stirred for 65 h at room temperature. After that, the mixture was diluted with cold water (240 mL) and extracted with tert-butyl methyl ether (1×180 mL, 5×90 mL). The combined organic extracts were washed with aqueous sodium carbonate solution (1 M, 90 mL) and brine (90 mL), dried over sodium sulfate and concentrated in vacuo to yield the title compound as a brown gum (22.05 g). The crude product (containing dimethylacetamide) was used in the next step without further purification. MS (EI): m/z=529.1 [M+H]$^+$. $^1$H NMR (CDCl$_3$, 400 MHz): δ 0.56-0.66 (m, 2H), 0.87-0.93 (m, 1H), 1.04-1.09 (m, 1H), 1.18-1.22 (m, 2H), 1.31 (s, 3H), 1.45-1.57 (m, 2H), 1.95-2.04 (m, 1H), 2.65 (s, 3H), 2.95-3.01 (m, 1H), 3.91 & 4.02 (ABX, J$_{AB}$=11.3 Hz, J$_{AX}$=5.6 Hz, J$_{BX}$=6.5 Hz, each 1H), 4.14-4.22 (m, 1H), 4.66 (dd, J=4.3 Hz, 8.1 Hz, 1H), 7.31 (dd, J=1.5 Hz, 5.3 Hz, 1H), 7.37 (bs, 1H), 7.69 & 7.80 (ABX, J$_{AB}$=8.2 Hz, J$_{AX}$=0 Hz, J$_{BX}$=2.0 Hz, each 1H), 7.93 (d, J=1.9 Hz, 1H), 8.06 (bs, 1H), 8.60 (d, J=5.1 Hz, 1H).

Step 2: (2S,4R)-1-(1-Methyl-cyclopropanecarbonyl)-4-[4-(2-methyl-pyridin-4-yl)-2-trifluoromethyl-benzenesulfonyl]-pyrrolidine-2-carboxylic acid (1-cyano-cyclopropyl)-amide

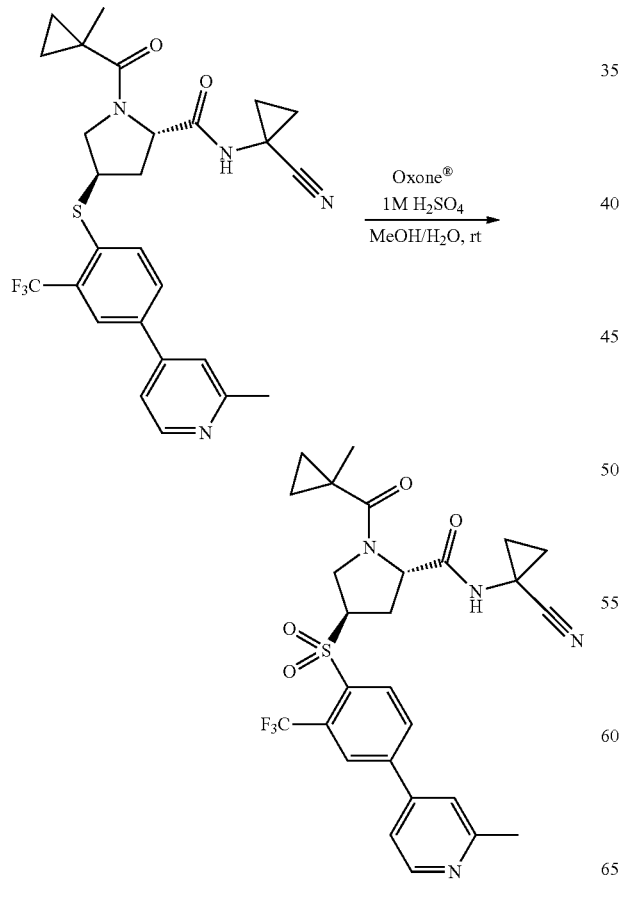

(2S,4R)-1-(1-Methyl-cyclopropanecarbonyl)-4-[4-(2-methyl-pyridin-4-yl)-2-trifluoromethyl-phenylsulfanyl]-pyrrolidine-2-carboxylic acid (1-cyano-cyclopropyl)-amide (crude product, containing dimethylacetamide, 90.2% purity m/m, 22.1 g, 37.7 mmol) was dissolved in methanol (70 mL) and sulfuric acid (1 M in water, 280 mL) at 0-5° C. (ice bath). Oxone® (73.5 g, 120 mmol) was added in one portion (slightly exotherm) and the mixture was stirred for 20 h at room temperature. Celite (7.5 g) was then added and the mixture was filtered. The precipitate was washed with water/methanol (4:1 v/v, 40 mL). Sodium metabisulfite (14.0 g, 73.6 mmol) was added in small portions to the combined filtrate (exotherm). Ethyl acetate (120 mL) was added and the pH of the biphasic mixture was adjusted to pH>8 by addition of an aqueous ammonia solution (25% m/m, 90 mL). After phase separation, the aqueous layer was extracted with ethyl acetate (2×120 mL). The combined organic extracts were washed with water/brine (1:1 v/v, 60 mL) and brine (60 mL), dried over sodium sulfate, and concentrated in vacuo at 55° C. The crude product (21.7 g) was dissolved in dichloromethane/methanol (100:3 v/v, 120 mL). Silica gel (40 g) was added and the slurry was filtered and washed with dichloromethane/methanol (100:3 v/v, 240 mL). The combined filtrates were concentrated in vacuo at 55° C. The residue, a white foam (18.1 g), was dissolved in ethanol (95 mL) at 70° C. and pre-warmed water (60-65° C., 135 mL) was added quickly. The clear solution was seeded and the resulting mixture was slowly cooled. The suspension was stirred for 5 h at room temperature and filtered. The precipitate was washed with ethanol/water (1:2 v/v, 50 mL) and n-heptane (50 mL) and dried in vacuo at 55° C. to yield the title compound as fine white powder (14.1 g, 71% over 2 steps). MS (ESI & APCI): m/z=561.2 [M+H]$^+$. $^1$H NMR (CDCl$_3$, 600 MHz): δ 0.62-0.67 (m, 1H), 0.74-0.80 (m, 1H), 1.08-1.15 (m, 2H), 1.15-1.21 (m, 2H), 1.38 (s, 3H), 1.46-1.54 (m, 2H), 2.27 (ddd, J=5.6 Hz, 8.4 Hz, 13.9 Hz, 1H), 2.69 (s, 3H), 2.77 (ddd, J=5.7 Hz, 8.4 Hz, 13.4 Hz, 1H), 3.93 (dd, J=7.6 Hz, 12.4 Hz, 1H), 4.21-4.27 (m, 1H), 4.73 (dd, J=3.9 Hz, 12.4 Hz, 1H), 4.78 (dd, J=5.0 Hz, 8.4 Hz, 1H), 7.36 (dd, J=1.4 Hz, 5.2 Hz, 1H), 7.41 (s, 1H), 7.89 (bs, 1H), 8.01 (dd, J=1.8 Hz, 8.2 Hz, 1H), 8.17 (d, J=1.5 Hz, 1H), 8.32 (d, J=8.3 Hz, 1H), 8.68 (d, J=5.2 Hz, 1H).

C6. Preparation of (2S,4R)-4-[4-(2-methyl-pyridin-4-yl)-2-trifluoromethyl-phenylsulfanyl]-1-(1-trifluoromethyl-cyclopropanecarbonyl)-pyrrolidine-2-carboxylic acid (1-cyano-cyclopropyl)-amide

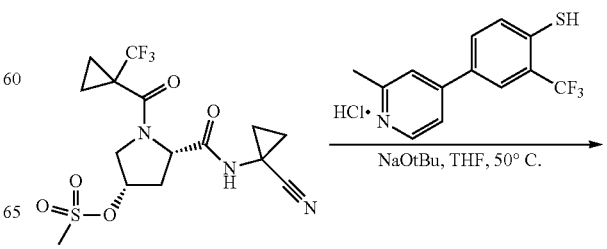

-continued

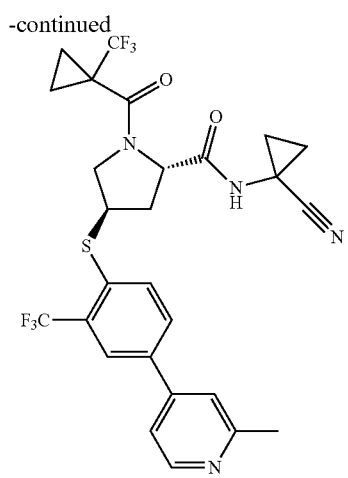

To a stirred suspension of methanesulfonic acid (3S,5S)-5-(1-cyano-cyclopropylcarbamoyl)-1-(1-trifluoromethyl-cyclopropanecarbonyl)-pyrrolidin-3-yl ester (20.5 g, 50 mmol) and 4-(2-methyl-pyridin-4-yl)-2-trifluoromethyl-benzenethiol hydrochloride (17.6 g, 57.5 mmol) in THF (75 mL) was added at 0° C. 25% sodium tert-butoxide in THF (43.2 g, 112.5 mmol) over 30 min and the reaction mixture was stirred at 50° C. for 4.5 h. After cooling to 10° C., the reaction mixture was added to dichloromethane (250 mL) and washed twice with deionized water (2×250 mL). The organic layer was dried ($Na_2SO_4$), filtered, and evaporated by rotary evaporation (45° C./≥10 mbar), affording the crude title product (30.9 g, 106%) as a beige, amorphous foam which was used without further purification in the next step. $^1$H NMR ($CDCl_3$, 400 MHz) δ 1.10-1.35 (m, 6H), 1.47-1.58 (m, 2H), 2.00-2.11 (m, 1H), 2.65 (s, 3H), 2.92-3.01 (m, 1H), 3.92 & 4.02 (ABC, $J_{AB}$=11.8 Hz, $J_{AC}$=5.0 Hz, $J_{BC}$=6.2 Hz, each 1H), 4.17 (quint, J=5.5 Hz, 1H), 4.72 (dd, $J_1$=8.1 Hz, $J_2$=4.8 Hz, 1H), 7.31 (dd, $J_1$=5.1 Hz, $J_2$=1.5 Hz, 1H), 7.37 (s, 1H), 7.62 (s, 1H), 7.66 (d, J=8.3 Hz, 1H), 7.80 (dd, $J_1$=8.1 Hz, $J_2$=1.9 Hz, 1H), 7.93 (d, J=2.1 Hz, 1H), 8.60 (d, J=5.1 Hz, 1H). ESI-MS (m/z) [M+H]$^+$ 583 (40).

The invention claimed is:
1. Process for the preparation of proline derivatives of formula I

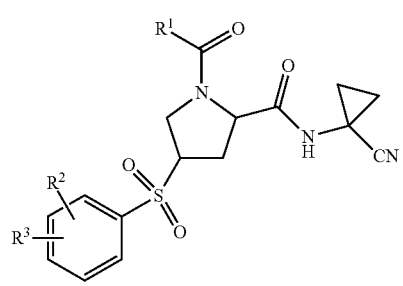

wherein,
$R^1$ is selected from $C_{1-7}$-alkyl or from

wherein $R^4$ is selected from $C_{1-7}$-alkyl, halogen-$C_{1-7}$-alkyl or from phenyl which is optionally substituted by halogen;
$R^2$ is selected from halogen or halogen-$C_{1-7}$-alkyl; and
$R^3$ is selected from hydrogen, halogen, halogen-$C_{1-7}$-alkyl, $C_{1-7}$-alkoxy, halogen-$C_{1-7}$-alkoxy or from a 5- or 6-membered heterocyclic ring containing one or two nitrogen atoms, the ring which is optionally substituted by $C_{1-7}$-alkyl or halogen;
comprising the steps
a) transforming an alcohol of formula II

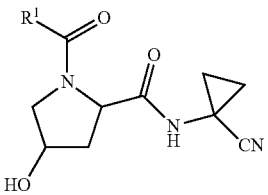

wherein $R^1$ has the meaning as above with a sulfonating agent in the presence of an organic solvent at a temperature of −10° C. to 40° C. into the sulfonate of the formula III

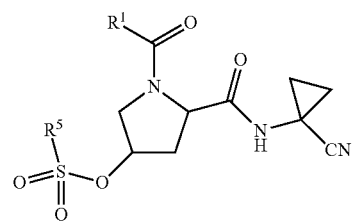

wherein $R^1$ has the meaning as above and $R^5$ is $C_{1-7}$-alkyl, halogen-$C_{1-7}$-alkyl or phenyl which is optionally substituted by $C_{1-7}$-alkyl, nitro or bromo
b) reacting the sulfonate of formula III with a thio compound of formula IV

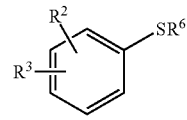

wherein $R^2$ and $R^3$ are as outlined above and $R^6$ is hydrogen or a protecting group in the presence of lithium-, sodium- or potassium tert-butylate in an organic solvent at temperatures between 10° C. and 90° C. to form the thioether of the formula V

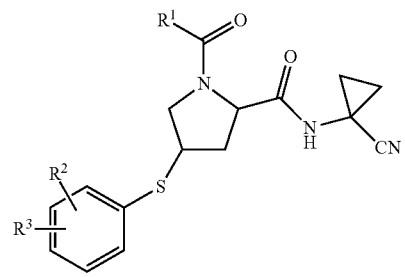

wherein $R^1$, $R^2$ and $R^3$ are as outlined above and c) oxidizing the thioether of formula V with an oxidating agent selected from peroxymonosulfate or magnesium monoperoxyphthalate hexahydrate in the presence of an organic solvent at temperature between 0° C. and 60° C. to form the proline derivative of formula I wherein $R^1$, $R^2$ and $R^3$ are as outlined above and wherein the process is further characterized in that the alcohol of formula II is prepared by a1) reacting a hydroxy proline ester of formula VI

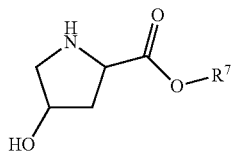

VI wherein $R^7$ is $C_{1-7}$-alkyl
with a carbonyl compound of formula VII $R^1COY$    VII wherein $R^1$ is as above and Y is halogen or OH to form a carbonyl proline ester of formula IX

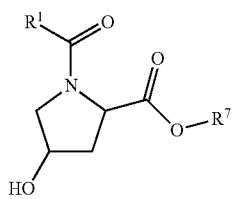

IX wherein $R^1$ and $R^7$ are as above;

b1) subsequent forming of a sulfonate of formula X

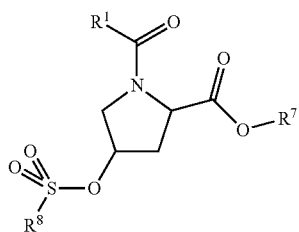

X wherein $R^1$ and $R^7$ are as above and $R^8$ is $C_{1-7}$-alkyl optionally substituted by halogen or phenyl which is optionally substituted by $C_{1-7}$-alkyl, nitro or bromo and c1) converting the sulfonate of formula X in the presence of an amino cyclopropane carbonitrile of formula XI

XI into the alcohol of formula II.

2. The process of claim 1, wherein $R^1$ is a residue of the formula

wherein $R^4$ is selected from $C_{1-7}$-alkyl, halogen-$C_{1-7}$-alkyl or from phenyl which is optionally substituted by halogen.

3. The process of claim 1, wherein
$R^2$ is selected from halogen or halogen-$C_{1-7}$-alkyl; and
$R^3$ is selected from halogen-$C_{1-7}$-alkoxy or from a 5- or 6-membered heterocyclic ring containing one or two nitrogen atoms, the ring which is optionally substituted by $C_{1-7}$-alkyl or halogen.

4. The process of claim 1, wherein the residue of the formula

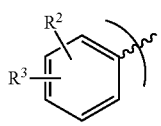

stands for

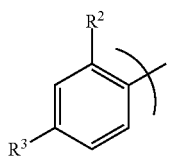

wherein $R^2$ and $R^3$ are as above.

5. The process of claim 1, wherein the proline derivatives of the formula I are chiral isomers of the formula

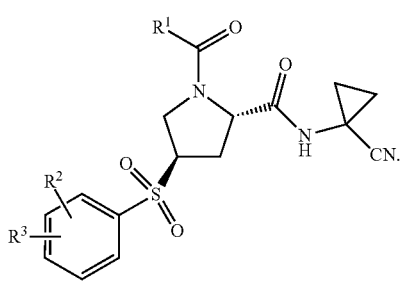

Ia

6. Process as in any one of claims 1 to 5, wherein the transformation in step a) is performed with a sulfonating agent in the presence of an organic solvent at temperature of −10° C. to 40° C.

7. Process as in any one of claims 1 to 5, wherein the reaction in step b) is performed in the presence of a base in an organic solvent at temperature between 10° C. and 90° C.

8. Process as in any one of claims 1 to 5, wherein the oxidation in step c) is performed with an oxidating agent in the presence of an organic solvent at temperature between 0° C. and 60° C.

9. The process of claim 1, wherein the oxidating agent is potassium peroxymonosulfate or magnesium monoperoxyphthalate hexahydrate.

10. The process of claim 1, wherein the alcohol of formula II is a chiral isomer of the formula

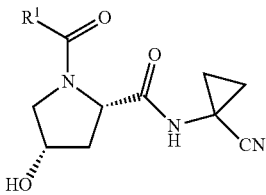

wherein $R^1$ has the meaning as above.

11. The process of claim 1, wherein the reaction in step a1) is performed in an organic solvent at temperatures between −10° C. and 25° C.

12. The process of claim 1, wherein the reaction in step b1) is performed with a sulfonating agent, in an organic solvent at temperatures between −10° C. and 40° C.

13. The process of claim 1, wherein the reaction in step c1) is performed in the presence of a carboxylate salt $NaR^{10}$=COO, wherein $R^{10}$=$C_{1-9}$-alkyl or aryl in a solvent at temperatures between 40° C. and 130° C.

14. The process of claim 13, wherein sodium 2-ethylhexenoate is used.

15. The process of claim 1, wherein the reaction in step a2) is performed in an organic solvent at temperatures between −10° C. and 25° C.

16. The process of claim 1 wherein the reaction in step b2) is performed in the presence of an alkali alkyl-or arylcarboxylate salt $MR^{10}COO$, wherein M is Li, Na, K or Cs and $R^{10}$ is $C_{1-9}$-alkyl or aryl in a solvent at temperatures between 40° C. and 130° C.

17. The process of claim 16, wherein sodium 2-ethylhexenoate is used.

18. The process of claim 1, wherein the alcohol of formula II is a chiral isomer of the formula

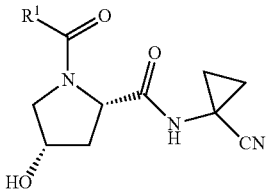

wherein $R^1$ has the meaning as above.

19. The process of claim 1, wherein the thio compound of formula IV

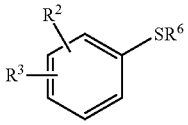

wherein $R^2$ and $R^3$ are as above and $R^6$ is hydrogen is prepared by a3) deprotecting a compound of formula XX

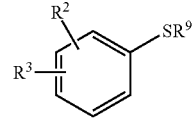

wherein $R^2$ and $R^3$ are as above and $R^9$ stands for a tertiary alkyl group of the formula

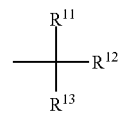

wherein $R^{11}$, $R^{12}$ and $R^{13}$ independently of each other stand for $C_{1-7}$-alkyl with an acid;
or by
b3) deprotecting a compound of formula XX

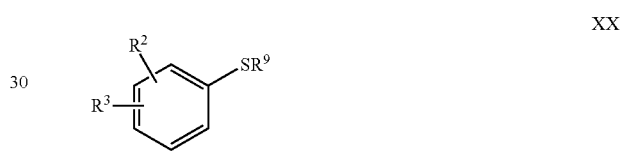

wherein $R^2$ and $R^3$ are as above and $R^9$ stands for trityl with trifluoro acetic acid in the presence of a reductive agent;
c3) lithiating a halogenated compound of formula XXI

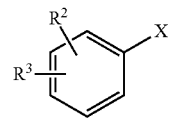

wherein $R^2$ and $R^3$ are as above and X stands for a halogen atom and a subsequent treatment with sulfur;
or by
d3) reacting a halogenated compound of formula XXI

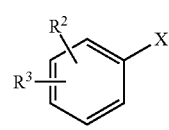

wherein $R^2$ and $R^3$ are as above and X stands for a halogen atom with a Grignard reagent and by a subsequent treatment with sulfur.

20. The process of claim 19, wherein $R^9$ in the compound of formula XX used for the reaction in step a3) is tert.butyl.

21. The process of claim 19, wherein the acid used in the reaction step a3) is selected from an aqueous mineral acid or an organic acid.

22. The process of claim 19, wherein the reductive agent used in the reaction step b3) is triethyl silane.

23. The process of claim 19, wherein the reaction in step c3) is performed with butyl lithium as lithiating agent in an organic solvent at temperatures between −80° C. to −20° C.

24. The process of claim 19, wherein the reaction with sulfur in step c3) is performed in an organic solvent at temperatures between −80° C. to −40° C.

25. The process of claim 19, wherein the reaction in step d3) is performed with a Grignard reagent selected from isopropyl magnesium chloride or from isopropyl magnesium chloride/lithium chloride in an organic solvent at temperature between 0° C. to 40° C.

26. The process of claim 19, wherein the reaction with sulfur in step d3) is performed in an organic solvent at temperatures between −20° C. to 20° C.

\* \* \* \* \*